(12) United States Patent
Che et al.

(10) Patent No.: US 10,577,387 B1
(45) Date of Patent: Mar. 3, 2020

(54) PLATINUM (II) COMPLEXES CONTAINING N-HETEROCYCLIC CARBENE LIGAND AND PINCER LIGANDS, SYNTHESIS, AND THEIR APPLICATIONS IN CANCER TREATMENT

(71) Applicant: THE UNIVERSITY OF HONG KONG, Hong Kong (CN)

(72) Inventors: Chi Ming Che, Mid-Level (HK); Sin Ki Fung, New Territories (HK); Tian Feng Chen, Guangzhou (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 16/059,679

(22) Filed: Aug. 9, 2018

(51) Int. Cl.
*C07F 15/00* (2006.01)
*A61P 35/00* (2006.01)
*G01N 33/574* (2006.01)
*G01N 21/64* (2006.01)

(52) U.S. Cl.
CPC .......... *C07F 15/0086* (2013.01); *A61P 35/00* (2018.01); *G01N 21/6458* (2013.01); *G01N 21/6486* (2013.01); *G01N 33/57415* (2013.01)

(58) Field of Classification Search
None
See application file for complete search history.

(56) References Cited

PUBLICATIONS

Wen et al. Phosphorescent square-planar platinum (II) complexes of 1,3-bis(2-pyridylimono)isoindoline with a monodentate strong-field ligand. Eur. J. Inorg. Chem. 2013, 4789-4798.*
Johnstone, et al., "The Next Generation of Platinum Drugs: Targeted Pt(II) Agents, Nanoparticle Delivery, and Pt (IV) Prodrugs", Chem. Rev. 116, Mar. 9, 2016, 3436-3486.
Wheate, et al. "The status of platinum anticancer drugs in the clinic and in clinical trials", Dalton Trans. Volume 39, No. 35, Sep. 21, 2010, pp. 8113-8127.
Jamieson, et al., "Structure, recognition, and processing of cisplatin-DNA adduct", Chem. Rev. 99, Apr. 29, 1999, 2467-2498.
Jung, et al., "Direct cellular responses to platinum-induced DNA damage", Chem. Rev. 107, vol. 107, No. 5, 2007, 1387-1407.
Housman, et al., "Drug Resistance in Cancer: An Overview", Cancers (Basel). 6, 1769-1792 (2014).
Kessenbrock, et al., "Matrix Metalloproteinases: Regulators of the Tumor Microenvironment", Cell. 141, Apr. 2, 2010, 52-67.
Whiteside, "The tumor microenvironment and its role in promoting tumor growth", Oncogene. Oct. 6, 2008, 27, 5904-5912.
Hicklin, et al.,"Role of the vascular endothelial growth factmor pathway in tumor growth and angiogenesis", J. Clin. Oncol. vol. 23, No. 5, Feb. 10, 2005, 1011-1027.
Ferrara, et al., "The biology of VEGF and its receptors", Nat. Med. vol. 9, No. 6, Jun. 2003, 669-676.

(Continued)

*Primary Examiner* — Anna Pagonakis
(74) *Attorney, Agent, or Firm* — Leason Ellis LLP

(57) ABSTRACT

Provided herein is a method of synthesis of Pt(II) complexes, a pharmaceutical composition comprises thereof. Also provided herein are the methods for the treatment and prevention of cancer/tumor in patients in need thereof by the administration of the Pt(II) complexes. Also provided is a method of detecting the Pt(II) complex in a biological system. Also provided is a method of making the Pt(II) complex The Pt(II) complexes possess anticancer activity such as the induction of cell death, inhibition of cellular proliferation, and inhibition of tumor growth in vivo.

4 Claims, 23 Drawing Sheets

Figure 2:
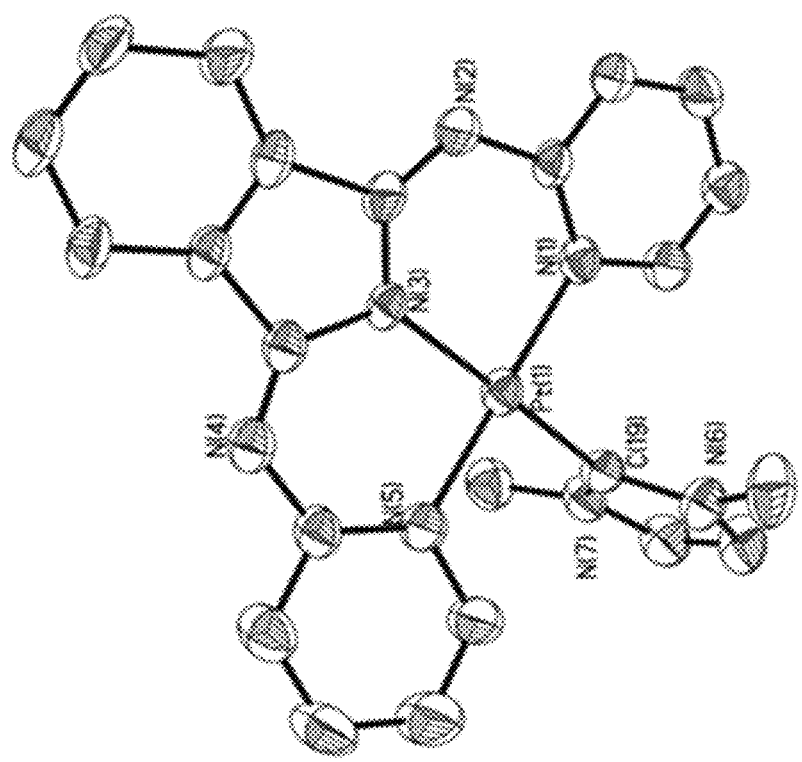

| $R^1$ | $-CH_3$ | $-C_4H_9$ | $-nC_6H_{13}$ | $-CH_3$ | $-CH_3$ | $-CH_2Ph$ | $-CH_2Ph$ |
|---|---|---|---|---|---|---|---|
| $R^2$ | $-CH_3$ | $-C_4H_9$ | $-nC_6H_{13}$ | $-C_8H_{17}$ | $-C_{16}H_{33}$ | $-CH_2Ph$ | $-C_4H_9$ |
| Complex | 1a | 1b | 1c | 1d | 1e | 1f | 1g |

(56) References Cited

PUBLICATIONS

Noh, et al., "Role of Urokinase Receptor in Tumor Progression and Development", Theranostics. vol. 3, Issue 7, 2013, 487-495.

Mehlen, et al., "Metastasis: a question of life or death", Nat. Rev. Cancer. vol. 6, Jun. 2006, 449-458.

Coussens, et al., "Matrix Metalloproteinase Inhibitors and Cancer—Trials and Tribulations", Science. vol. 295, Mar. 29, 2002, 2387-2392.

Kenny, et al., "Targeting the tumor microenvironment", Front Biosci. 12, Mar. 17, 2010, 3468-3474.

Vacca, et al., "Inhibition of endothelial cell functions and of angiogenesis by the metastasis inhibitor NAMI-A", British J. of Cancer. 86, 2002, 993-998.

Nazarov, et al., "Ruthenium clusters as new class of anti-angiogenic agent", J. Biol. Inorg. Chem. 19, 2014, S647-S647.

Nowak-Sliwinska, et al., "Organometallic ruthenium(II) arene compounds with antiangiogenic activity", Journal of Medicinal Chemistry, 54, 2011, 3895-3902.

Liu, et al., "A rhodium(III) complex inhibits LPS-induced nitric oxide production and angiogenic activity in cellulo", Journal of Inorganic Biochemistry, 140, 2014 23-28.

Ott, et al., "A Gold(I) Phosphine Complex Containing a Naphthalimide Ligand Functions as a TrxR Inhibiting Antiproliferative Agent and Angiogenesis Inhibitor" J. Med. Chem. 52, 2009, 763-770.

Pavic, et al., "Mononuclear gold(III) complexes with phenanthroline ligands as efficient inhibitors of angiogenesis: A comparative study with auranofin and sunitinib", Journal of Inorganic Biochemistry, 174, 2017, 156-168.

Wilbuer, et al., "Iridium complex with antiangiogenic properties. Angew", Chem. Int. Ed. 49, 2010, 3839-3842.

Zamora, et al., "Dual Antitumor and Antiangiogenic Activity of Organoplatinum(II) Complexes", Journal of Medicinal Chemistry, 58, 2015, 1320-1336.

Zamora, et al., "Exploring the Influence of the Aromaticity on the Anticancer and Antivascular Activities of Organoplatinum(II) Complexes", Chem.-Eur J. 23, 2017, 5614-5624.

Shojaei, et al., "Role of the microenvironment in tumor growth and in refractoriness/resistance to anti-angiogenic therapies", Drug Resistance Updates 11, 2008, 219-230.

Gasparini, et al. "Combination of Antiangiogenic Therapy With Other Anticancer Therapies: Results, Challenges, and Open Questions" Journal of Clinical Oncology, vol. 23, No. 6, Feb. 20, 2005, 1295-1311.

Zhang, et al., "A dual cytotoxic and antiangiogenic water-soluble gold(III) complex induces endoplasmic reticulum damage in HeLa cells", Chem. Commun. 48, 2012, 3388-3390.

Sun, et al., "Luminescent cyclometalated platinum(II) complexes containing N-heterocyclic carbene ligands with potent in vitro and in vivo anti-cancer properties accumulate in cytoplasmic structures of cancer cells", Chemical Science, 2, 2011, 728-736.

Visbal, et al., "N-heterocyclic carbene metal complexes: photoluminescence and applications", Chem. Soc. Rev. 43, 2014, 3551-3574.

Wen, et al., "Spectroscopic and Luminescence Studies on Square-Planar Platinum(II) Complexes with Anionic Tridentate 3-Bis(2-pyridylimino)isoindoline Derivatives", Inorganic Chemistry, 49, 2010, 2210-2221.

Wen, et al., "Luminescent square-planar platinum(II) complexes with tridentate 3-bis(2-pyridylimino)isoindoline and monodentate N-heterocyclic ligands", Dalton Transactions, 40, 2011, 6929-6938.

Hanson, et al., "A Paradigm for Blue- or Red-Shifted Absorption of Small Molecules Depending on the Site of π-Extension", J. Am. Chem. Soc. 132, 2010, 16247-16255.

Che, et al., "Metal complexes in medicine with a focus on enzyme inhibition" Curr. Opin. Chem. Biol., 2010, 14, 255-261.

Healy, et al., "Targeting the endoplasmic reticulum-stress response as an anticancer strategy", Eur. J. Pharmacol. 625, 2009, 234-246.

Lai, et al., "Endoplasmic reticulum stress: signaling the unfolded protein response" Physiology. 22, 2007, 193-201.

Smiley, et al., "Intracellular Heterogeneity in Mitochondrial Membrane Potentials Revealed by a J-Aggregate-Forming Lipophilic Cation JC-1", Proc. Natl. Acad. Sci. U. S. A. vol. 88, May 1991, 3671-3675.

Sun, et al., "Decreased expression of CHIP leads to increased angiogenesis via VEGF-VEGFR2 pathway and poor prognosis in human renal cell carcinoma", Scientific Reports. 5, 2015, 9774.

Shiao, "The von Hippel-Lindau gene and protein in tumorigenesis and angiogenesis: a potential target for therapeutic designs", Current Medicinal Chemistry, 2003, 10, 2461-2470.

Liang, et al., "The C-Kit Receptor-Mediated Signal Transduction and Tumor-Related Diseases", International Journal of Biological Sciences, 2013, vol. 9, 435-443.

Kessenbrock, et al., "Matrix Metalloproteinases: Regulators of the Tumor Microenvironment", Cell. 141, Apr. 10, 2010, 52-67.

Hwang, et al., "Tissue inhibitor of metalloproteinase-1 is responsible for residual pleural thickening in pleural tuberculosis", Tohoku. J. Exp. Med. 2015, 235, 327-333.

Gondi, et al., "Down-regulation of uPAR and uPA activates caspase-mediated apoptosis and inhibits the PI3K/AKT pathway", Int. J. Oncol. 31, Jul. 2007, 19-27.

Vial, et al., "ERK-MAPK signaling coordinately regulates activity of Rac1 and RhoA for tumor cell motility", Cancer Cell. Jul. 2003, vol. 4, 67-79.

Walker, et al., "Structural Determinants of Phosphoinositide 3-Kinase Inhibition by Wortmannin, LY294002, Quercetin, Myricetin, and Staurosporine", Molecular Cell, vol. 6, Oct. 2000, 909-919.

Marampon, et al., "MEK/ERK inhibitor U0126 affects in vitro and in vivo growth of embryonal rhabdomyosarcoma", Mol. Cancer. Ther. 8, Mar. 2009, 543-551.

Hicklin, et al., "Role of the vascular endothelial growth factor pathway in tumor growth and angiogenesis", J. Clin. Oncol. vol. 23, No. 5, Feb. 10, 2005 1011-1027.

Ferrara, et al., "The biology of VEGF and its receptors", Nature Medicine, vol. 9, No. 6, Jun. 2003, 669-676.

Plouet, et al., "Extracellular cleavage of the vascular endothelial growth factor 189- amino acid form by urokinase is required for its mitogenic effect", J. Biol. Chem. vol. 272, No. 20, May 1997, 13390-13396.

Rodriguez-Manzaneque, et al., "Thrombospondin-1 suppresses spontaneous tumor growth and inhibits activation of matrix metalloproteinase-9 and mobilization of vascular endothelial growth factor", Proc. Natl. Acad. Sci. vol. 98, No. 22, Oct. 23, 2001, 12485-12490.

Mira, et al., "Secreted MMP9 promotes angiogenesis more efficiently than constitutive active MMP9 bound to the tumor cell surface", J. Cell. Sci. 117, 2004, 1847-1857.

Arnaoutova, et al., "In vitro angiogenesis: endothelial cell tube formation on gelled basement membrane extract", Nature Protocols, vol. 5, No. 4, 2010, 628-635.

Wen, et al., "Spectroscopic and Luminescence Studies on Square-Planar Platinum(II) Complexes with Anionic Tridentate 3-Bis(2-pyridylimino)isoindoline Derivatives", Inorganic Chemistry, 2010, vol. 49, No. 5, 2210-2221.

Zubarev, et al., "Identification of dominant signaling pathways from proteomics expression data", J. Proteomics 2008, 71, 89-96.

Lau, et al., "Dysregulation of clathrin promotes thyroid cell growth and contributes to multinodular goiter pathogenesis", Biochimica et Biophysica Acta, Mol. Basis Dis. 2015, 1852, 1676-1686.

Bruijnincx, et al., "New Trends for Metal Complexes with Anticancer Activity", Curr. Opin. Chem. Biol., Apr. 12, 2008, 12, 197-206.

Sun, et al., "Some uses of transition metal complexes as anti-cancer and anti-HIV agents", Dalton Trans., 2007, 4884-4892.

Wang, et al., "Cellular Processing of Platinum Anticancer Drugs" Nature Reviews, Drug Discovery, Apr. 2005, vol. 4, 307-320.

Rosenberg, et al. "Platinum compounds: a new class of potent antitumour agents." Nature 222.5191, 1969, 385.

Fichtinger-Schepman, et al. "cis-Diamminedichloroplatinum (II)-induced DNA adducts in peripheral leukocytes from seven cancer patients: quantitative immunochemical detection of the adduct

(56) References Cited

PUBLICATIONS induction and removal after a single dose of cis-diamminedichloroplatinum (II)." Cancer research 47.11, 1987, 3000-3004.
Baik, et al. "Theoretical study of cisplatin binding to purine bases: why does cisplatin prefer guanine over adenine?." Journal of the American Chemical Society 125.46, 2003, 14082-14092.
Anderson, et al. "Hetero-multinuclear ruthenium (III)/platinum (II) complexes that potentially exhibit both antimetastatic and antineoplastic properties." Inorganic chemistry 51.23, 2012, 12917-12924.
Muscella, et al. "Sublethal concentrations of the platinum (II) complex [Pt (O, O'-acac)(y-acac)(DMS)] alter the motility and induce anoikis in MCF-7 cells." British journal of pharmacology 160.6, 2010, 1362-1377.
Rademaker-Lakhai, et al. "A phase I and pharmacological study with imidazolium-trans-DMSO-imidazole-tetrachlororuthenate, a novel ruthenium anticancer agent." Clinical Cancer Research 10.11, 2004, 3717-3727.
Yang, et al. "Interaction between 8-hydroxyquinoline ruthenium (II) complexes and basic fibroblast growth factors (bFGF): inhibiting angiogenesis and tumor growth through ERK and AKT signaling pathways." Metallomics 6.3, 2014, 518-531.
Feng, et al. "Structurally sophisticated octahedral metal complexes as highly selective protein kinase inhibitors." Journal of the American Chemical Society 133.15, 2011, 5976-5986.
Sun, et al. "Dual anti-angiogenic and cytotoxic properties of ruthenium (III) complexes containing pyrazolato and/or pyrazole ligands." Dalton Transactions 48, 2009, 10712-10716.
Nazarov, et al. "Synthesis and characterization of a new class of anti-angiogenic agents based on ruthenium clusters" Scientific reports 3, 2013, 1485.

\* cited by examiner

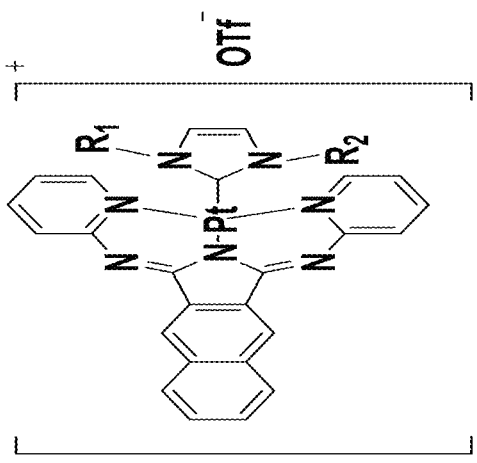
FIG. 1B
| Complex | 1a | 1b | 1c | 1d | 1e | 1f | 1g |
|---|---|---|---|---|---|---|---|
| R$^1$ | –CH$_3$ | –C$_4$H$_9$ | –nC$_6$H$_{13}$ | –CH$_3$ | –CH$_3$ | –CH$_2$Ph | –CH$_2$Ph |
| R$^2$ | –CH$_3$ | –C$_4$H$_9$ | –nC$_6$H$_{13}$ | –C$_8$H$_{17}$ | –C$_{16}$H$_{33}$ | –CH$_2$Ph | –C$_4$H$_9$ |
FIG. 1F
| Complex | 1j |
|---|---|
| R$^1$ | –CH$_2$Ph |
| R$^2$ | –CH$_2$Ph |
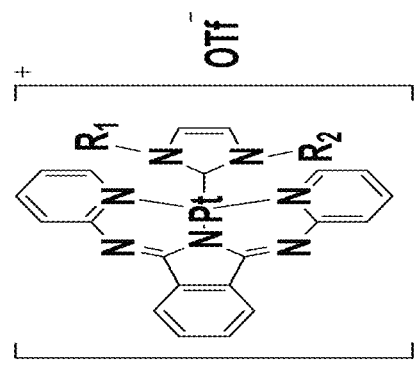
FIG. 1A
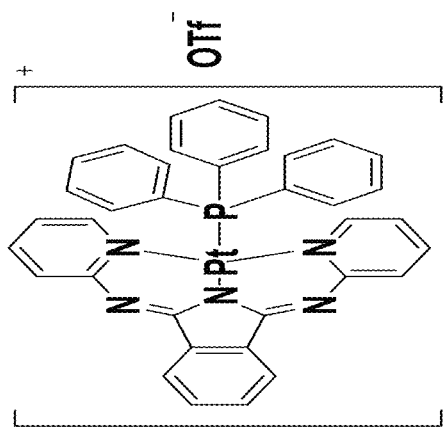
FIG. 1C, FIG. 1D, FIG. 1E

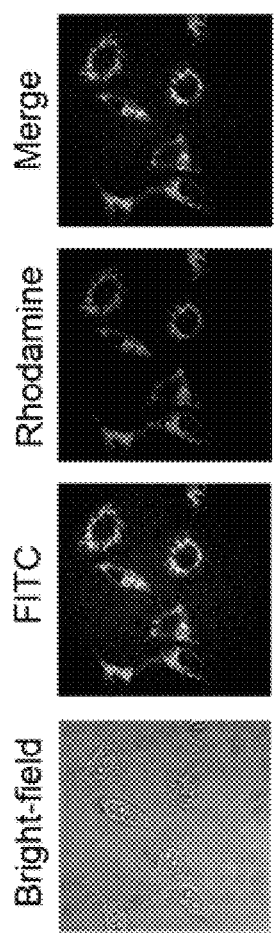
FIG. 4A
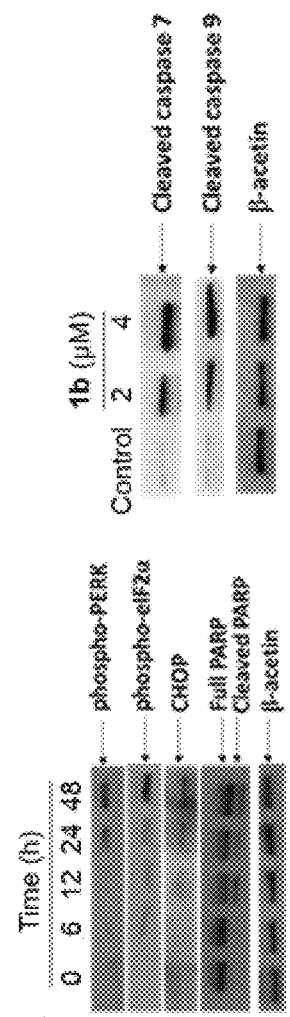
FIG. 4C
FIG. 4B

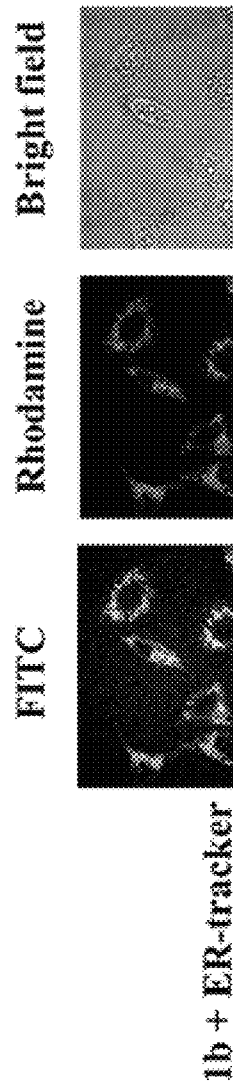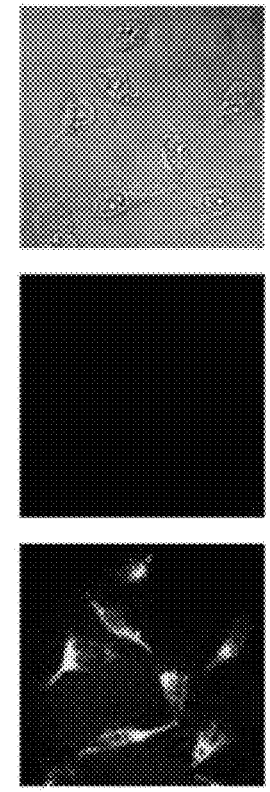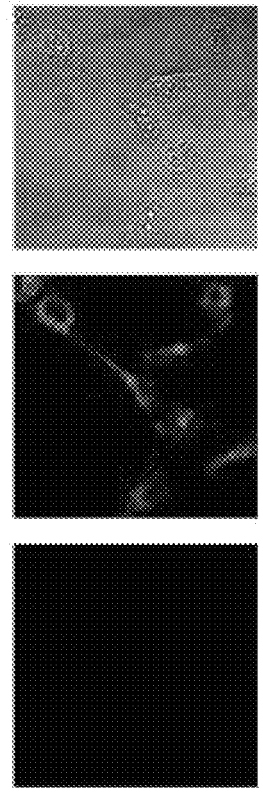

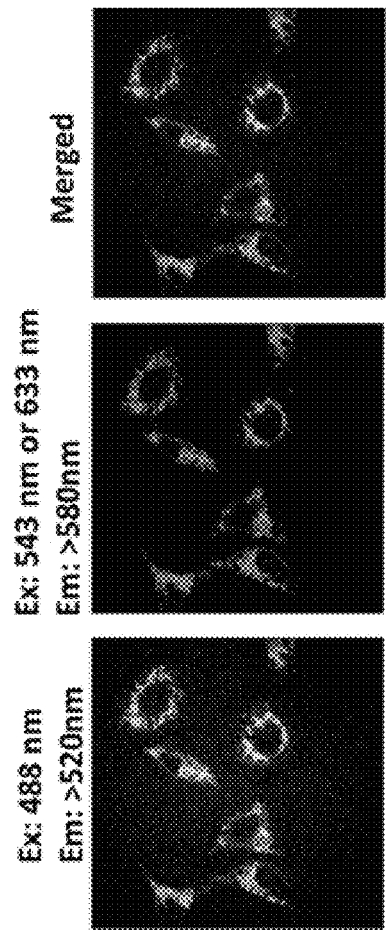
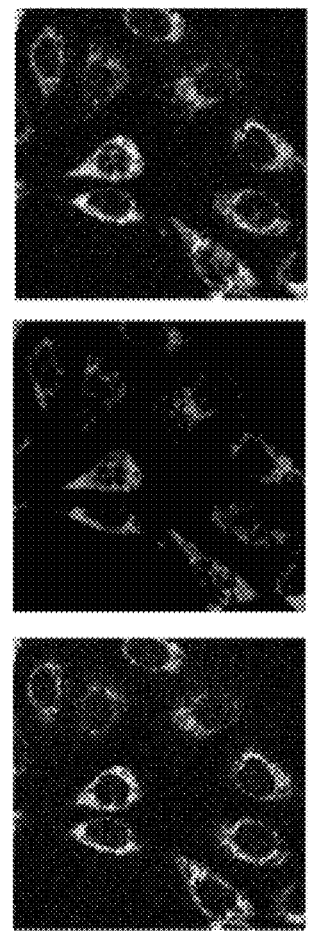
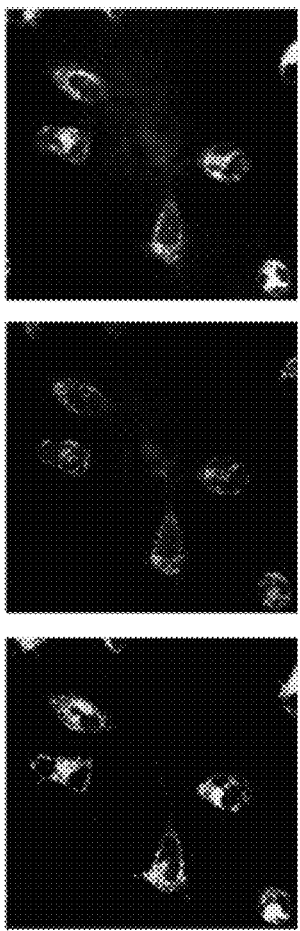

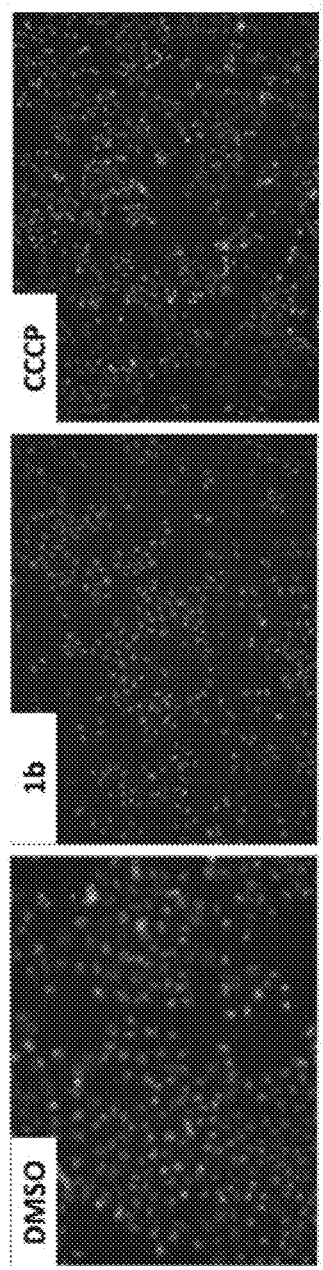
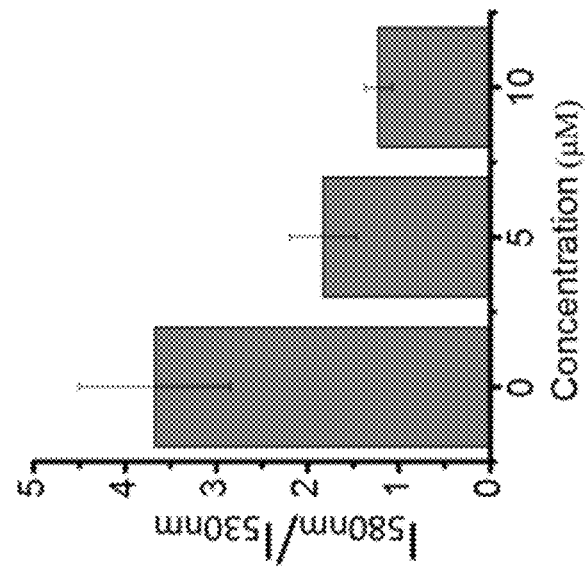
FIG. 8A  FIG. 8B  FIG. 8C  FIG. 8D

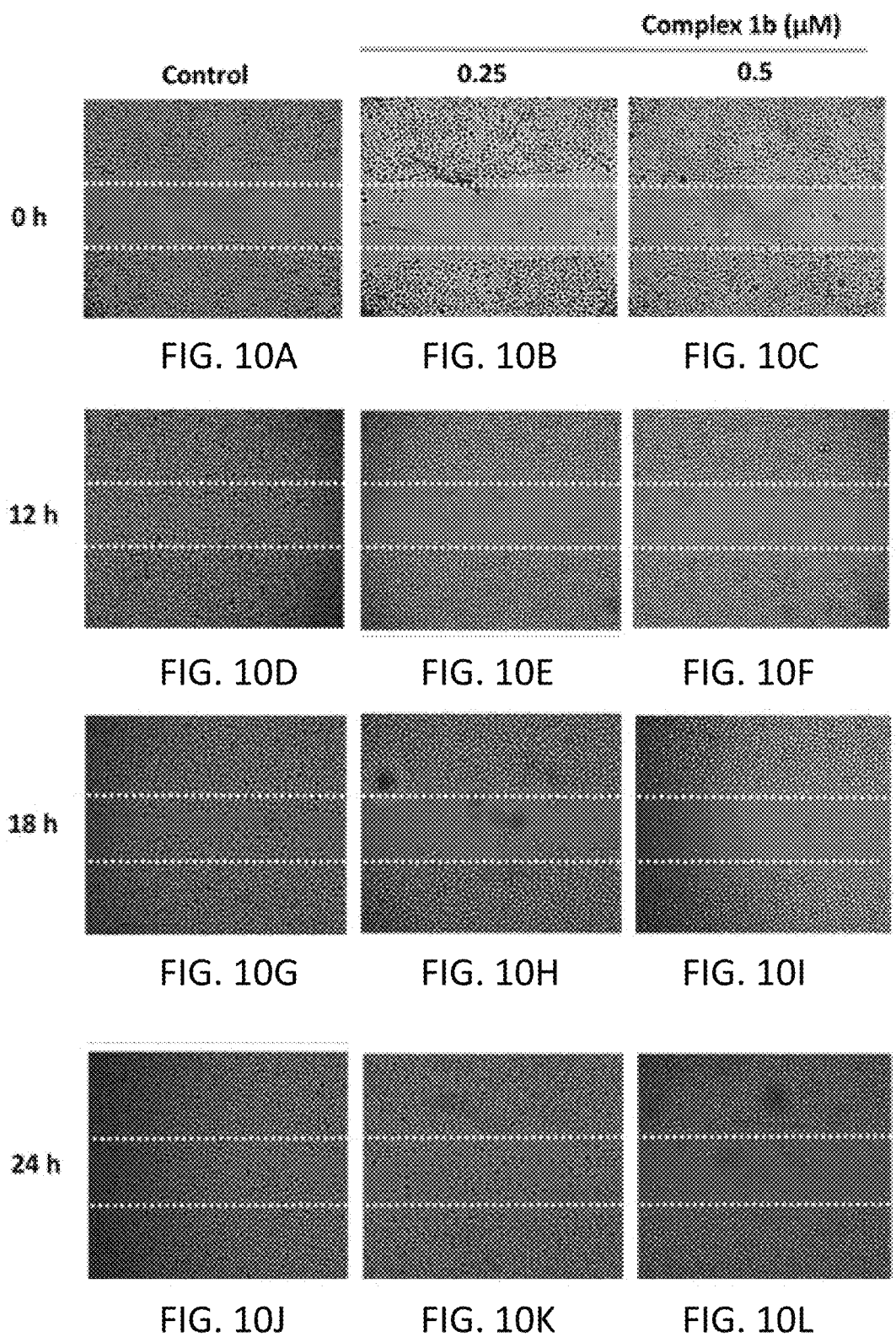

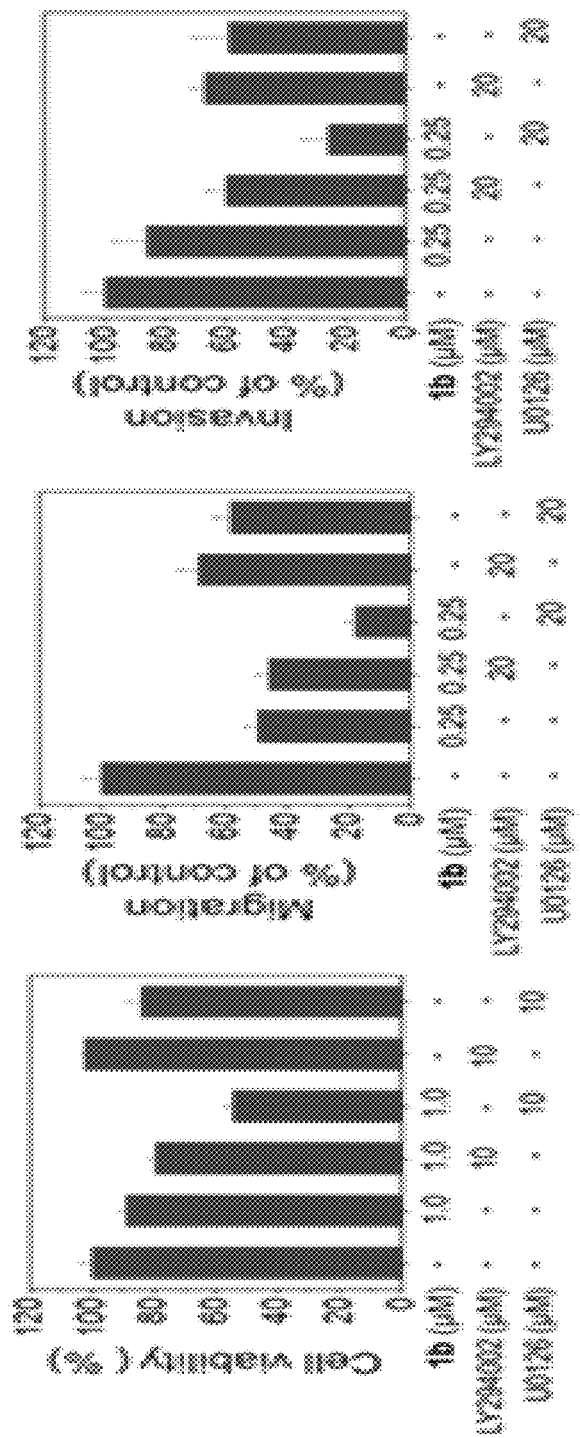

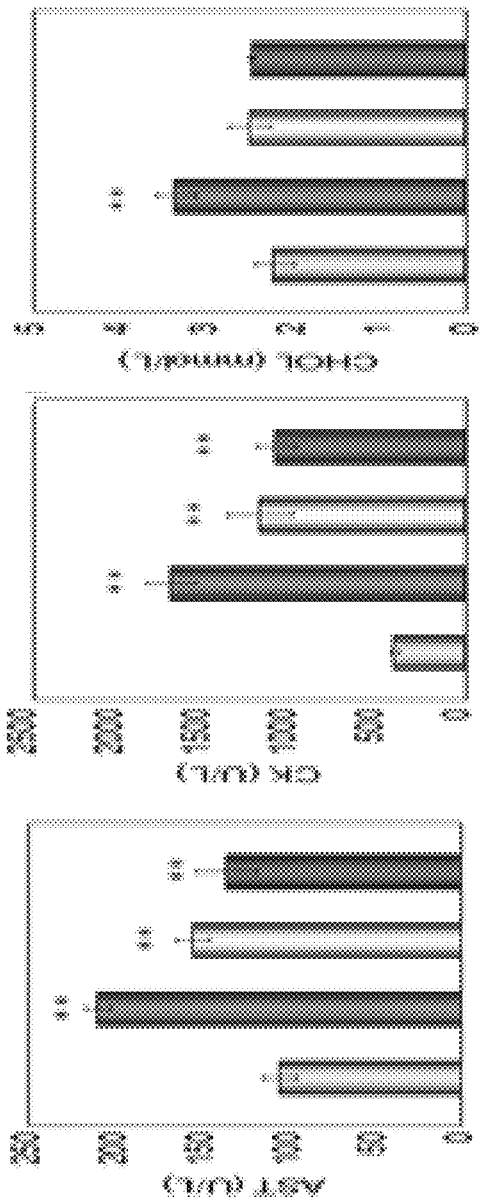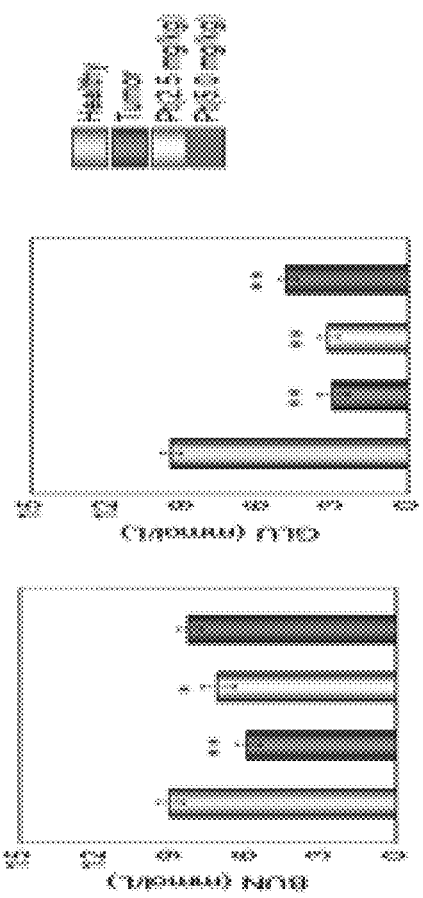

PLATINUM (II) COMPLEXES CONTAINING N-HETEROCYCLIC CARBENE LIGAND AND PINCER LIGANDS, SYNTHESIS, AND THEIR APPLICATIONS IN CANCER TREATMENT

1. INTRODUCTION

Described herein are platinum (II) complexes containing N-heterocyclic carbene ligand, a method of synthesis of the platinum (II) complexes containing N-heterocyclic carbene ligand, methods of treating and preventing cancer or tumor using the platinum (II) complexes containing N-heterocyclic carbene ligand. The platinum (II) complexes has a dual action including cytotoxic to tumor growth and anti-angiogenesis. Also provided is a method of detecting the platinum (II) complexes containing N-heterocyclic carbene ligand by fluorescence microscopy. Also described are therapeutic and prophylactic compositions containing a purified platinum(II) complexes containing N-heterocyclic carbene ligand. In certain embodiments, the methods of treating and preventing cancer or tumor are in combination with other cancer or tumor treatment. In certain embodiments, the cancer or tumor treatment is chemotherapy, radiation therapy, gene therapy, surgery or a combination thereof.

2. BACKGROUND

As stimulated by the clinical success of cis-diamminedichloroplatinum (cisplatin), a platinum(II) complex, for the treatment of cancers, scientists have paid great attention to the development of metal-based anticancer drugs which target DNA including the cisplatin analogues and some ruthenium(II)-arene complexes [Sadler, P. J. et al. Curr. Opin. Chem. Biol. 2008, 12, 197]. However, severe side effects and the induced drug resistance are commonly encountered and thus subsequently have hampered the wider applications of these DNA binding agents.

Cisplatin and its derivatives are widely used as chemotherapeutic agents for treating cancer. Yet, most of them fail in combating with metastatic cancer, which is a big problem found in cancer treatment. In view of this, it is important to develop new cytotoxic agents that can at the same time regulate tumor microenvironment which is important for governing tumor progression, growth, angiogenesis and metastasis.

3. SUMMARY

Described herein are Pt(II)-NHC-BPI complexes, compositions comprising Pt(II)-NHC-BPI complexes, methods of using the Pt(II)-NHC-BPI complexes in cancer/tumor treatment, a method of synthesis of Pt(II)-NHC-BPI complexes, and a method of detecting the Pt(II)-NHC-BPI complexes. In one embodiment, the method of treatment and prevention is in combination with one or more cancer/tumor therapies.

Described herein is a Pt(II) complex comprising a Pt(II)-NHC ligand and 1, 3-bis(2-pyridylimino) isoindoline (BPI) ligand, wherein the Pt(II)-NHC ligand is perpendicular to the BPI ligand.

In one embodiment, the NHC ligand and the BPI ligand have a bond angle of about 90°. In one embodiment, the Pt(II) complex has anti-tumor or anti-angiogenic properties.

Described herein is a method of making a Pt(II) complex, comprising reacting [Pt(BPI)Cl] with corresponding imidazolium salt in the presence of a base to form the Pt(II) complex.

In one embodiment, provided herein is a method for cancer or tumor treatment and prevention resulting in induction of cell death, inhibition of cellular proliferation, inhibition of angiogenesis, or inhibition of in vivo tumor growth. In one embodiment, provided herein is a method comprising administering to a subject in need thereof a composition comprising an effective amount of a Pt(II)-NHC-BPI complex. In one embodiment, the Pt(II)-NHC-BPI complexes is a platinum(II) complex described herein represented by the structural formulae of I, derivatives thereof; or a pharmaceutically acceptable salt, solvate, or hydrate thereof,

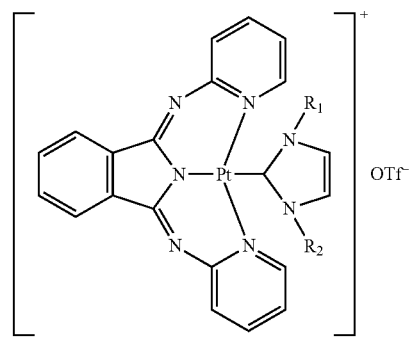

wherein $R^1$ is —$CH_3$, —$C_4H_9$, -$nC_6H_{13}$, —$CH_3$, or —$CH_2Ph$, and wherein $R^2$ is —$CH_3$, —$C_4H_9$, -$nC_6H_{13}$, —$C_8H_{17}$, —$C_{16}H_{33}$, or —$CH_2Ph$. In another embodiment, provided herein is a method for detecting an effective amount of the Pt(II)-NHC-BPI complexes, depending on the fluorescence changes at proper wavelength. The Pt(II)-NHC-BPI complex is a platinum(II) complex described herein can be represented by the structural formula of I, or an acceptable salt thereof,

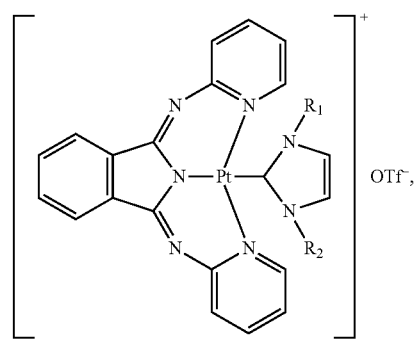

wherein $R^1$ is —$CH_3$, —$C_4H_9$, -$nC_6H_{13}$, —$CH_3$, or —$CH_2Ph$, and wherein $R^2$ is —$CH_3$, —$C_4H_9$, -$nC_6H_{13}$, —$C_8H_{17}$, —$C_{16}H_{33}$, or —$CH_2Ph$.

Described herein is a Pt(II) complex which comprises a Pt(II)-NHC ligand and 1, 3-bis(2-pyridylimino) isoindoline (BPI) ligand, wherein the Pt(II)-NHC ligand is perpendicular to the BPI ligand, and having the following formula:

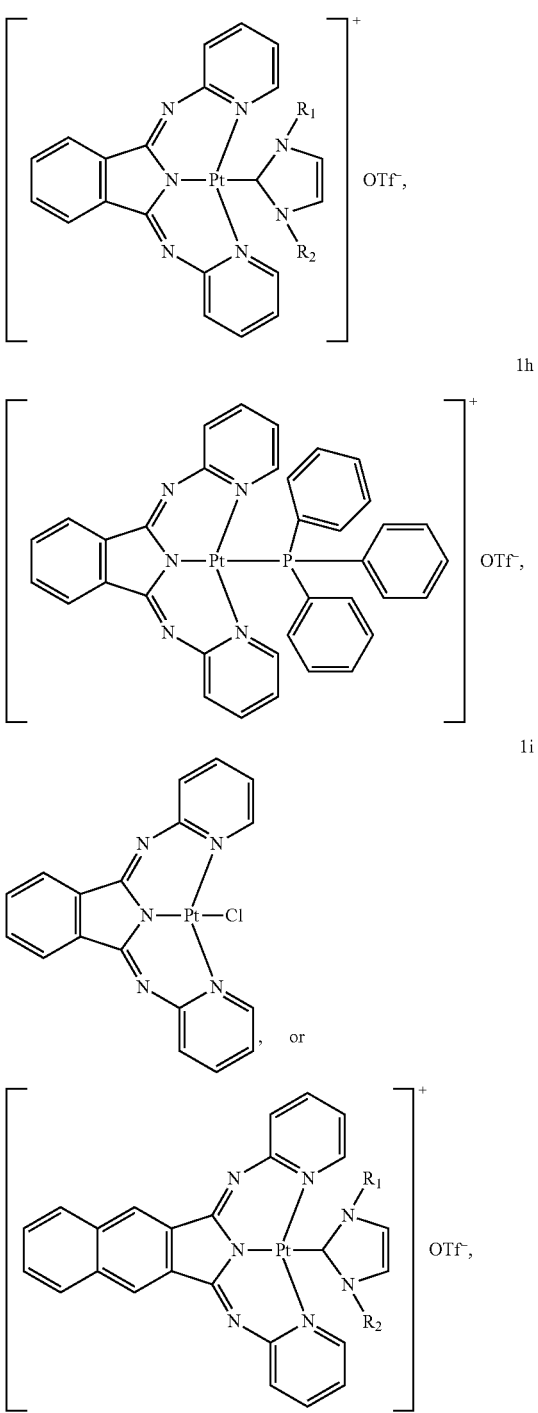

wherein R[1] is —CH$_3$, —C$_4$H$_9$, -nC$_6$H$_{13}$, —CH$_3$, or —CH$_2$Ph, and wherein R[2] is —CH$_3$, —C$_4$H$_9$, -nC$_6$H$_{13}$, —C$_8$H$_{17}$, —C$_{16}$H$_{33}$, or —CH$_2$Ph. In one embodiment, R[1] is C$_4$H$_9$ and R[2] is C$_4$H$_9$.

Described herein is a composition comprising a Pt(II)-NHC-BPI complex, which comprises a Pt(II)-NHC ligand and 1, 3-bis(2-pyridylimino) isoindoline (BPI) ligand, wherein the Pt(II)-NHC ligand is perpendicular to the BPI ligand.

In one embodiment, the NHC ligand and the BPI ligand have a bond angle of about 90°. In one embodiment, the Pt(II) complex comprises anti-tumor and/or anti-angiogenic properties.

Described herein is a method for treatment of tumor or cancer in a subject comprising administering to a subject in need thereof an effective amount of a composition comprising a Pt(II) complex that regulates uPA/uPAR-mediated angiogenic pathway or VEGF-induced angiogenic pathway. In one embodiment, provided herein is a method wherein the tumor is one or more of hepatocellular carcinoma, cervical epithelioid carcinoma, lung carcinoma, breast cancer, colon cancer, melanoma or nasopharyngeal carcinoma. In one embodiment, the effective amount is about 0.1 mg/kg to 50 mg/kg. In one embodiment, the effective amount is about 2.5-5 mg/kg.

The Pt(II)-NHC-BPI complexes are stable in air and aqueous solutions like phosphate-buffered saline (PBS) conditions. The anti-cancer active Pt(II)-NHC-BPI complexes is also accompanied with the release of highly fluorescent ligand. The Pt(II)-NHC-BPI complexes display similar anti-cancer or anti-tumor activity. They can be detected via the fluorescent ligand which makes them to be excellent bio-probes and for prevalent biological applications.

Described herein is a method to detect the Pt(II) complex in a subject, said method comprises administering an effective amount of Pt(II) complex to the subject and detect the Pt(II) complex using fluorescent detection. In one embodiment, the effective amount of Pt(II) complex is 1 µM-500 µM.

4. BRIEF DESCRIPTION OF THE DRAWINGS

FIGS. 1(A)-(F) show Chemical structures of the Pt(II) complexes 1a-1j.

FIG. 2 shows perspective views of X-ray crystal structure of 1a, showing bond angle (C$_{19}$—Pt$_1$—N$_5$) of 90.6°.

Figure 3B:
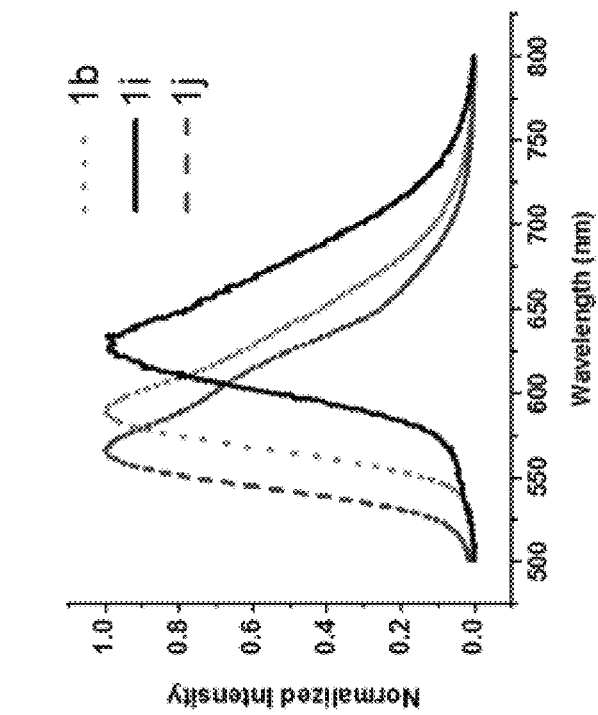
Figure 3A:
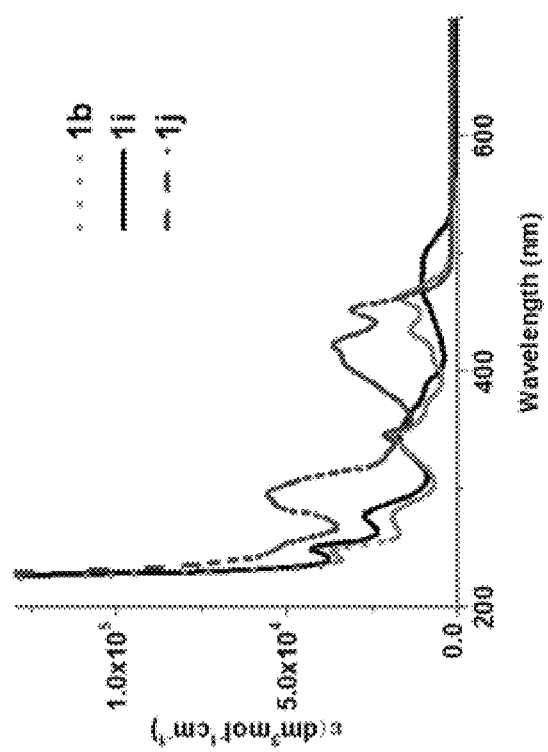

FIGS. 3(A)-(B) show (A) Absorption and (B) Normalized emission spectra of 1b, 1i and 1j in degassed CH$_2$Cl$_2$.

FIGS. 4(A)-(C) show (A) Confocal fluorescence microscopy images of HeLa cells incubated with 1b (5 µM) for 15 min, and subsequently co-stained with ER-Tracker™. (B) Western blot analysis of expression levels of ER stress-related proteins in MDA-MB-231 cells treated with 1b (5 µM) for indicated time. (C) Western blot analysis of apoptosis-related proteins after treating MDA-MB-231 cells with indicated concentration of 1b for 24 h.

FIGS. 5(A)-(I) show confocal fluorescence microscopy images of HeLa cells incubated with 1b, ER-Tracker™, or both, taken using FITC or Rhodamine filters.

FIGS. 6(A)-(I) show co-localization analysis of 1b with ER-Tracker™ (upper panel), Mitotracker® (middle) and Lysotracker® (lower panel).

Figure 7A:
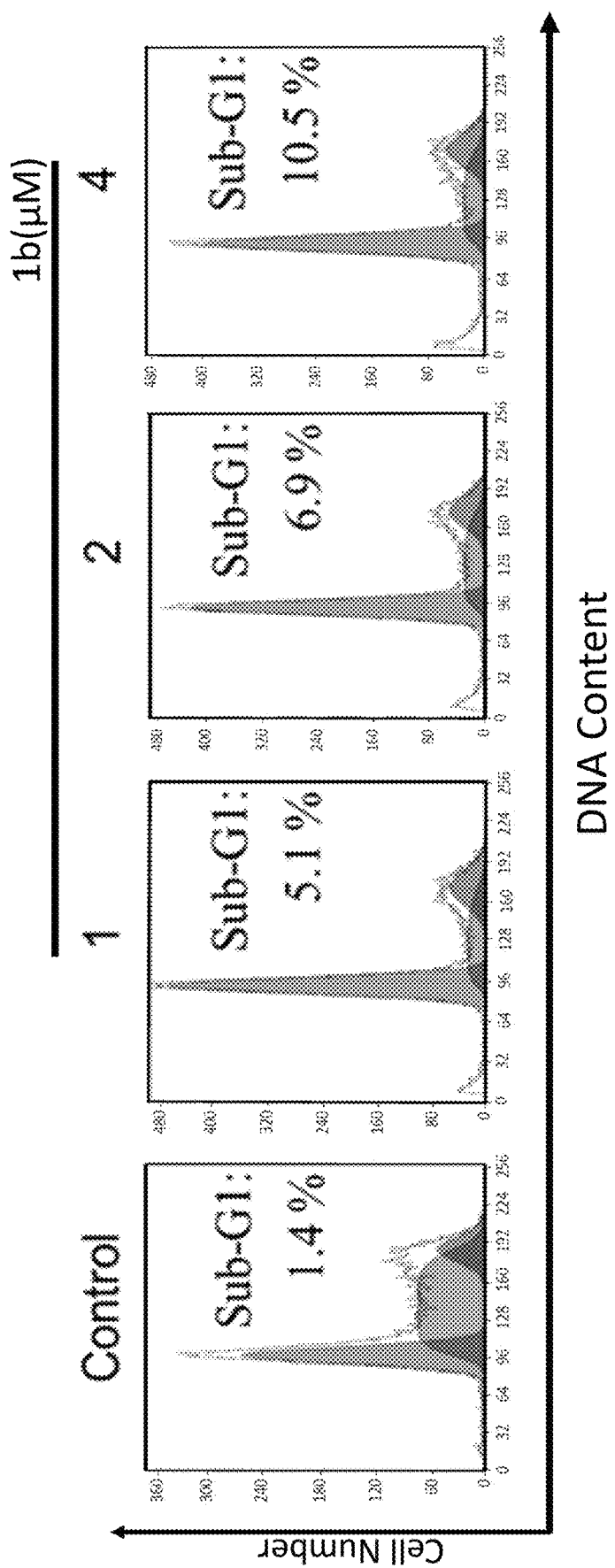
Figure 7B:
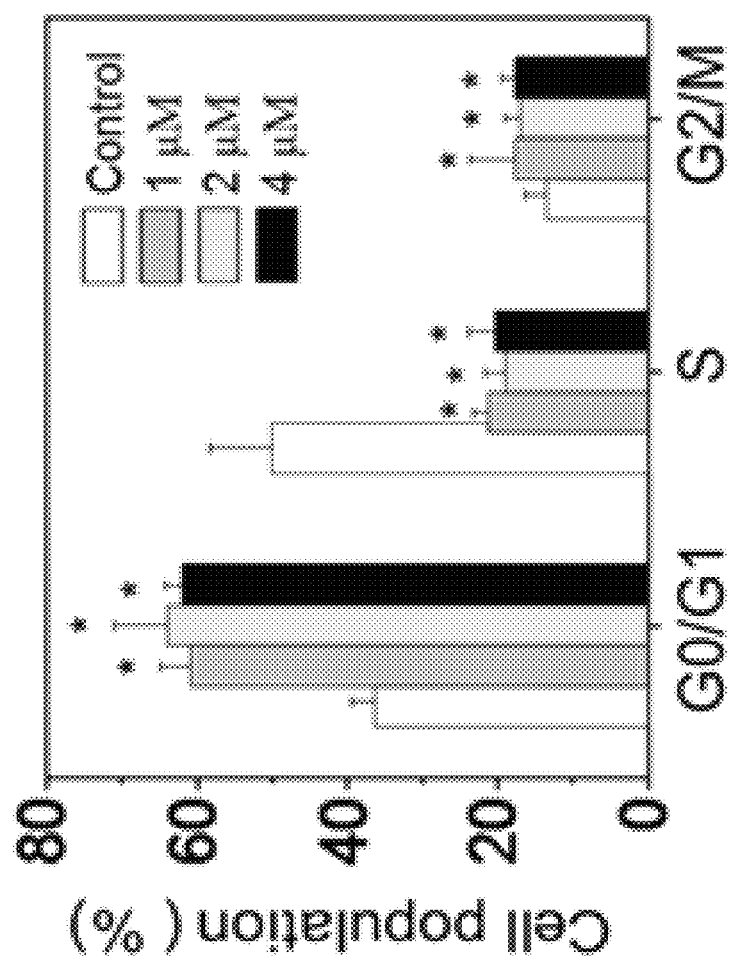
Figure 7C:
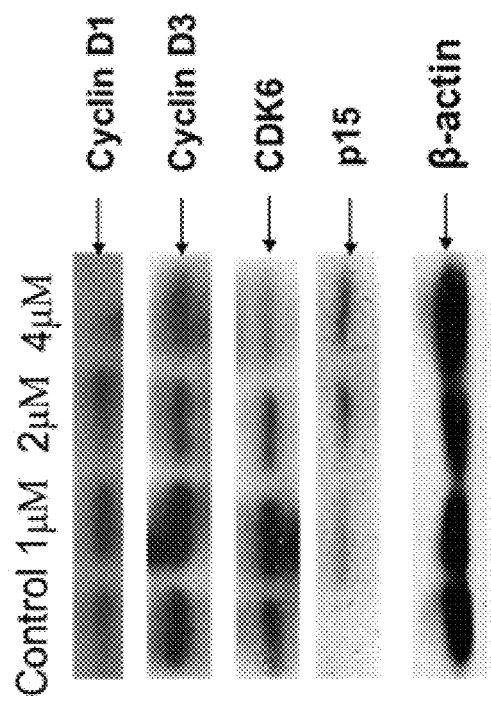

FIGS. 7(A)-(C) show (A), (B) Effects of 1b on cell apoptosis and cell cycle of MDA-MB-231 cells, as determined by flow cytometry. Cells were treated with indicated concentrations of 1b for 24 h. *, p<0.05 versus the control. (C) Western blot analysis of expression levels of G0/G1 phase-related proteins in MDA-MB-231 cells after treatment with indicated concentrations of 1b for 24 h.

FIGS. 8(A)-(D) show JC1 staining of HeLa cells. (A)-(C) HeLa cells were treated with DMSO vehicle, 1b (5 µM) and CCCP (carbonyl cyanide m-chlorophenyl hydrazine, a mitochondrial membrane potential disrupter; 50 µM) for 2 h, and examined using fluorescence microscope with excitation at 470 nm. (D) JC1 fluorescence intensity ratio of $I_{580nm}/I_{530nm}$ after treatment of HeLa cells with 1b at different concentrations.

Figure 9B:
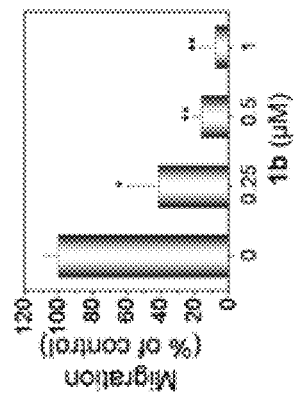
Figure 9D:
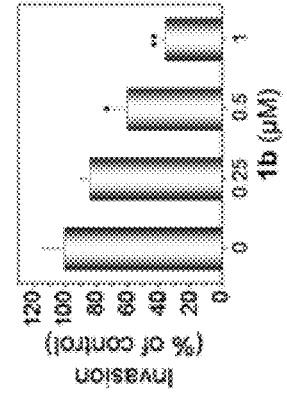
Figure 9A:
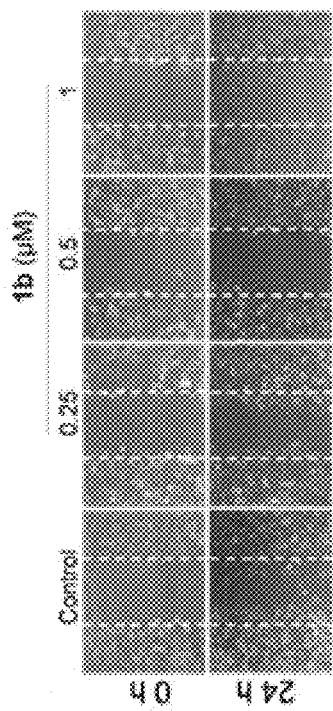
Figure 9C:
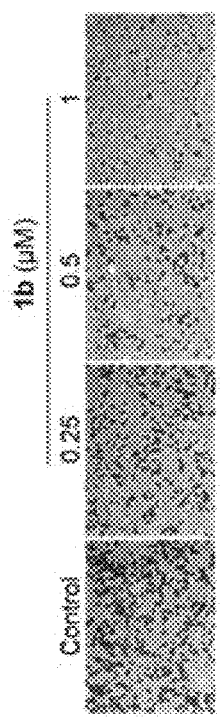

FIGS. 9(A)-(B) show wound closure assay to determine the effect of 1b on migration of MDA-MB-231 cells. FIGS. 9(C)-(D) Transwell invasive assay to determine the effect of 1b on invasion of MDA-MB-231 cells after 24 h treatment. The cells were imaged by a phase-contrast microscope (200×, Nikon TS 100). The migrated and invaded cells were quantified by manual counting and inhibition ratio was expressed as % of control (n=3; *, p<0.05; **, p<0.01 versus the control).

FIGS. 10(A)-(L) show inhibition of MDA-MB-231 cells migration by different concentrations of 1b at different time points.

Figure 11:
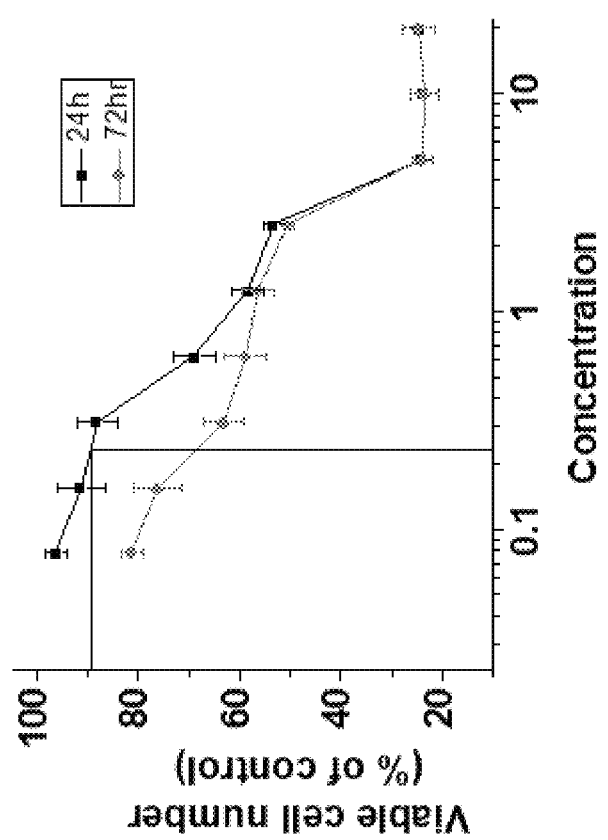

FIG. 11. shows the viability of MDA-MB-231 cells treated with 1b for the indicated time intervals.

Figure 12A:
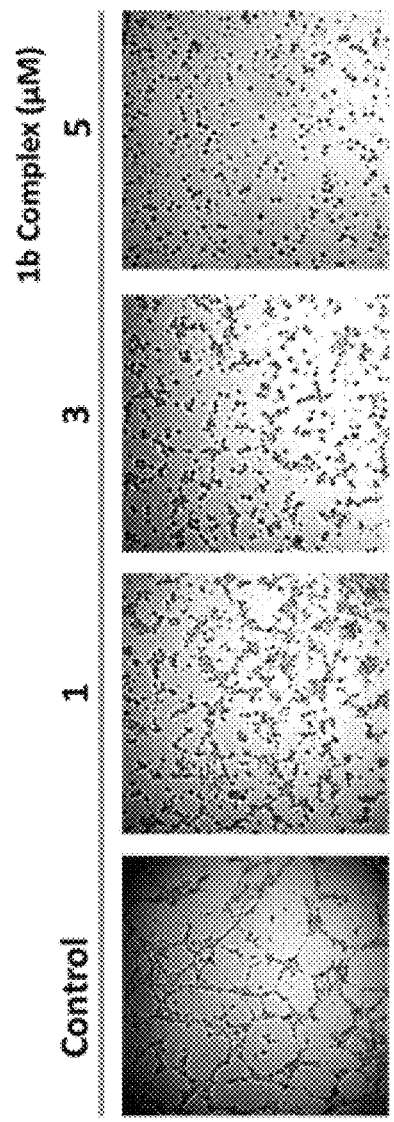
Figure 12B:
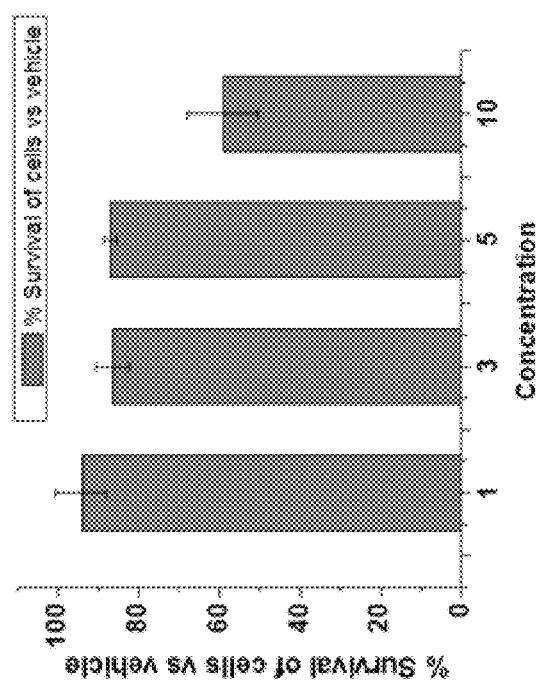

FIGS. 12(A)-(B) show (A) Tube formation assay of MS1 cells treated with different concentrations of 1b for 3 h. (B) MTT assay on MS1 cells after treatment with 1b for 3 h, revealing no significant cell death at 1, 3 and 5 aM of 1b.

FIGS. 13(A)-(G) show (A) Western blotting analysis of expression levels of uPA, MMP-9 and TIMP1 in MDA-MB-231 cells treated with different concentrations of 1b for 24 h. (B) Western blotting analysis of expression levels of uPAR and MMP-9 in MDA-MB-231 cells treated with 1b (2 µM) for different time intervals. (C-D) Effects of 1b on expression levels of phosphorylated and total FAK, ERK and Akt. Cells were exposed to (C) different concentrations of 1b for 24 h or (D) 1b (2 µM) with different incubation times. (E)-(G)) Effects of 1b, LY294002 and U0126 on inhibition of MDA-MB-231 cells (C) growth, (F) migration and (G) invasion. For co-treatment experiments, cells were pretreated with LY294002 or U0126 (10 or 20 µM) for 1 h and co-treated with 1b for another 24 h. All data are expressed as means±SD of triplicates.

FIGS. 14(A)-(F) show (A) Effects of 1b on secretion of intracellular VEGF in MDA-MB-231 cells. Cells were exposed to different concentrations of 1b for 24 h. (B)-(D) 1b inhibited VEGF-induced HUVECs growth, migration and invasion. HUVECs were cultured in MDA-MB-231 conditioned medium (CM, VEGF=13.4 ng/ml) and exposed to different concentrations of 1b for 24 h. The treatment group with VEGF (50 ng/ml) was regarded as positive control. (E) 1b inhibited VEGF-induced tube formation of HUVECs. Cells were pre-coated with matrigel and treated with different concentrations of 1b for 24 h. (F) Effect of 1b on ex vivo angiogenesis as determined by CAM assay. All data are expressed as means±SD of triplicates. Bars with different characters (A)-(D) are statistically different at p<0.05 level.

FIGS. 15(A)-(H) show (A) The tumor volume of MDA-MB-231-bearing mice after treatment by saline, Pt (5 mg/kg), Pt (2.5 mg/kg), respectively. n=10, *P<0.05, **P<0.01. (B) The weights of MDA-MB-231-bearing mice after treatment by saline, Pt (5 mg/kg), Pt (2.5 mg/kg), respectively (n=10). (C) Ki67, CD34 and Cleaveage-caspase-3 expression and TUNEL-DAPI co-staining assay of tumor tissues after treatment with Pt (2.5 mg/kg and 5.0 mg/kg). (D)-(H) Blood biochemistry data including liver-function markers: AST, heart-function markers: CK, blood fat: CHOL, kidney-function markers: BUN and blood glucose: GLU. n=3, *P<0.05, **P<0.01.

Figure 16:
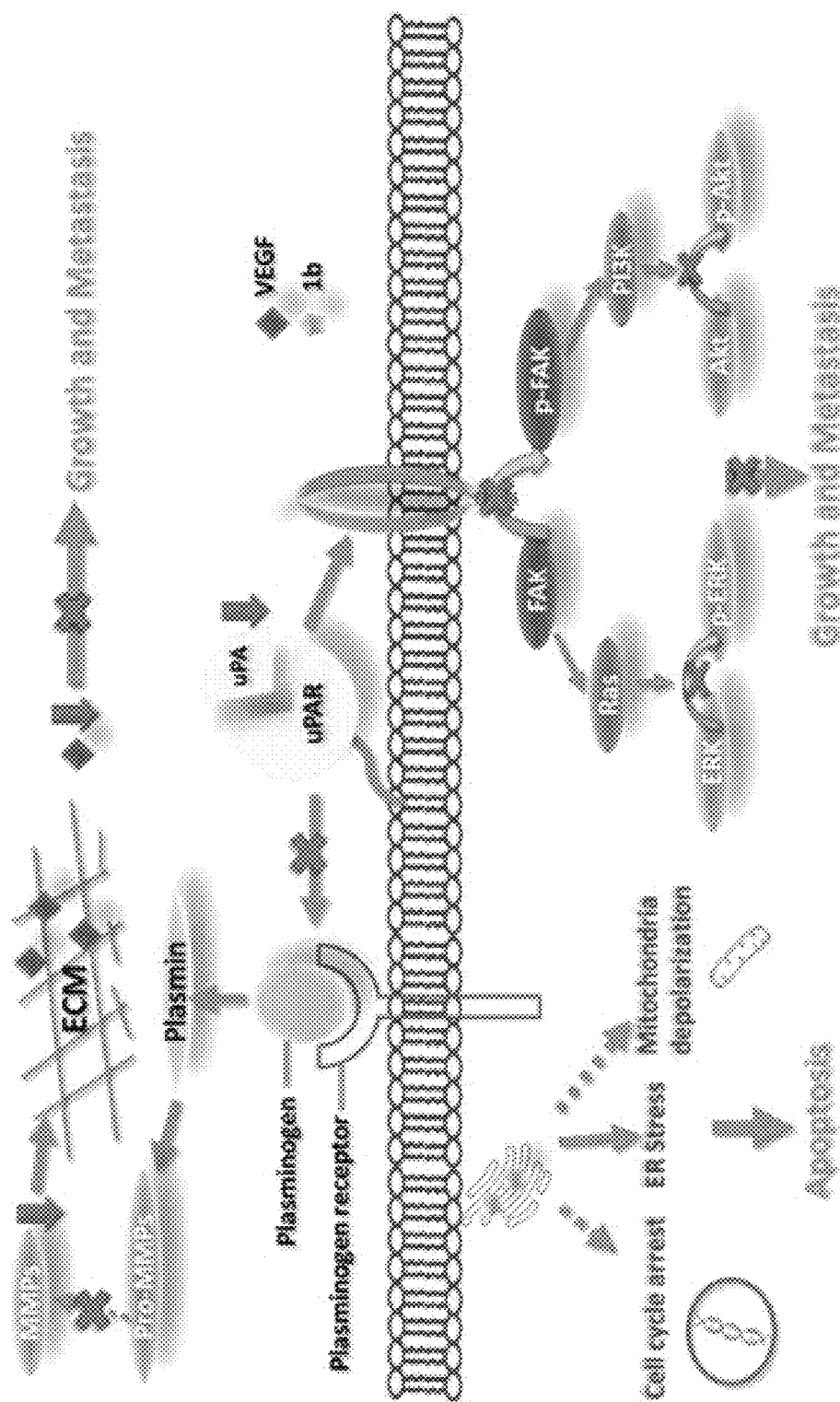

FIG. 16 shows proposed anti-apoptotic and anti-angiogenic pathways by 1b.

5. DETAILED DESCRIPTION

Provided herein is a new series of dual cytotoxic and anti-angiogenic platinum(II) complexes with N-heterocylic carbene (NHC) and 1,3-bis(2-pyridylimino)isoindoline (BPI) ligands. The NHC ligand is found to be perpendicular to the plane of BPI ligand, as revealed by X-ray crystallography, thus allowing these platinum(II) complexes to target other biomolecules rather than DNA only. The introduction of NHC ligand, which is a strong σ-donor, also renders the complexes strong luminescence in aqueous solution and live cells, and hence their subcellular localization in endoplasmic reticulum (ER) can be identified by fluorescence microscopy. With their accumulation in ER, they are found to induce ER stress and subsequent apoptotic cell death, accounting for their potent potent cytotoxicity toward cancer cells.

5.1 Pt(II) Complexes

Platinum(II) compounds as exemplified by cisplatin and its derivatives have been widely used in the treatment of cancer.[1,2] Their mechanism of action is mainly through covalent crosslinking onto DNA, leading to cancer cell apoptosis or cell cycle arrest.[3,4] Since DNA is the primary molecular target, cancer cells with changes in repair of DNA lesion, such as enhanced nucleotide excision repair or deficiency in mismatch repair, are found to show resistance to these platinum drugs.[5] Moreover, these platinum drugs generally give rise to severe toxic side effects, probably due to the fact that DNA is not a specific biomolecule in cancer cells.[5] As a result, there are continuing efforts on searching metal complexes with new working mechanisms.

It should be advantageous for developing anticancer drugs to target tumor microenvironment. Tumor microenvironment is complex and dynamic, and is regulated by a number of mediators and signaling transduction pathways that govern tumor progression including tumor initiation, growth, angiogenesis and metastasis.[6,7] For example, tumor cells developing their microenvironment by secretion of vascular endothelial growth factor (VEGF) or cytokines to promote abnormal tumor neovasculature formation, which provides nutrients for further tumor growth and metastasis.[8,9] In addition, binding of urokinase plasminogen activator (uPA) to uPA receptor (uPAR) in tumor microenvironment can trigger activation of metalloproteinases (MMPs) to degrade the components of surrounding extracellular matrix (ECM),[10] and hence contributes to tumor cell metastasis. Together with the fact that over 90% of cancer deaths today are due to metastasis formation,[11] regulations of tumor microenvironment including inhibition of tumor growth, metastasis and VEGF-induced angiogenesis, have been considered as effective means in combating tumor progression.[12,13]

A number of metal complexes have been reported to target tumor microenvironment by acting as angiogenesis inhibitors.[14-16] Notably, a ruthenium(III) complex, NAMI-A, was found to be non-cytotoxic toward solid tumor but show promising antitumor activities by inhibition of tumor metastasis and angiogenesis.[14] In addition, platinum complexes showing dual cytotoxic and anti-angiogenic properties have also been explored,[17-19] and they should show improved anticancer efficacy through decreasing acquired-drug resistance and systemic toxicities, as compared to that of a cytotoxic or an anti-angiogenic agent alone.[20,21] However, none of them exhibited promising in vivo antitumor and anti-angiogenic activities.

Disclosed herein are platinum(II) complexes that exhibit dual cytotoxic and anti-angiogenic properties, and are luminescent in vitro so that real-time monitoring of therapeutic progress would be feasible. Provided is an out-of-plane ancillary ligand to the platinum(II) center for targeting biomolecules other than DNA in order to achieve dual cytotoxic and anti-angiogenic properties. NHC is a strong G-donor and can increase the energy level of non-emissive ligand-field (LF) state, rendering platinum(II) complexes strongly luminescent,[24] and this strong luminescence feature can help to elucidate mechanism of anticancer actions of the complexes by fluorescence microscopy. Provided is a new series of platinum(II) complexes containing NHC ligands and 1,3-bis(2-pyridylimino)isoindoline (BPI) which has two accessible nitrogen atoms ([Pt(BPI)(NHC)](OTf); FIG. 1). Platinum(II) complexes with BPI and chloride or triphenylphosphine ligand was also prepared. The complexes were found to exhibit dual cytotoxic and anti-angiogenic activities, as revealed by proteomic data and biochemical assays, as well as in vivo and ex vivo experiments.

Provided herein is a Pt(II)-NHC-BPI complex. In one embodiment, the Pt(II)-NHC-BPI complexes is a platinum (II) complex described herein represented by the structural formulae of I, derivatives thereof; or a pharmaceutically acceptable salt, solvate, or

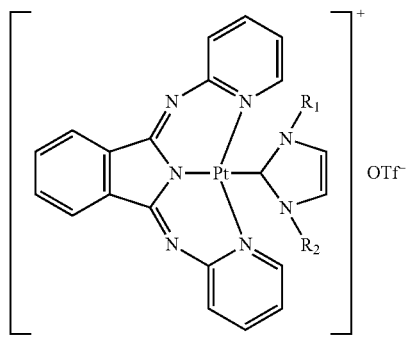

hydrate thereof, wherein $R^1$ is —$CH_3$, —$C_4H_9$, -$nC_6H_{13}$, —$CH_3$, or —$CH_2Ph$, and wherein $R^2$ is —$CH_3$, —$C_4H_9$, -$nC_6H_{13}$, —$C_8H_{17}$, —$C_{16}H_{33}$, or —$CH_2Ph$. Described herein is a Pt(II) complex which comprises a Pt(II)-NHC ligand and 1, 3-bis(2-pyridylimino) isoindoline (BPI) ligand, wherein the Pt(II)-NHC ligand is perpendicular to the BPI ligand, and having the following formula:

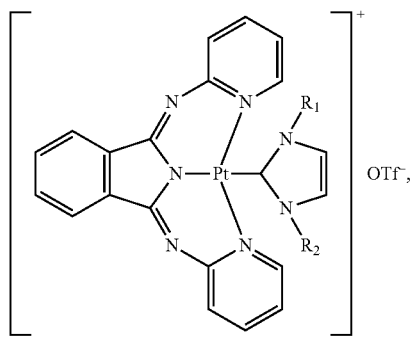

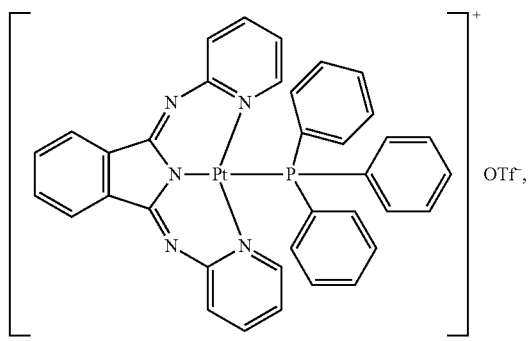

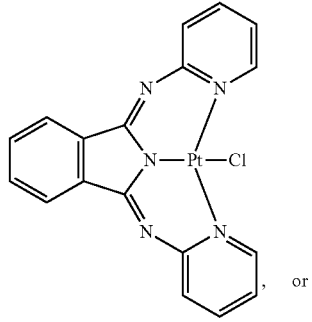

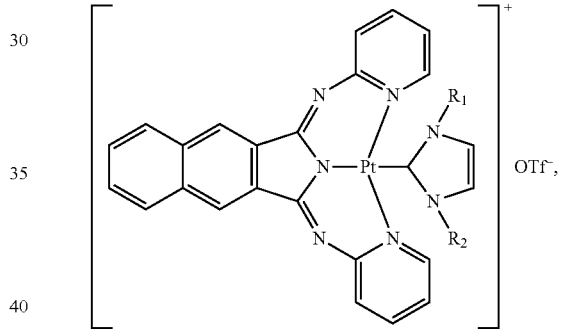

wherein $R^1$ is —$CH_3$, —$C_4H_9$, -$nC_6H_{13}$, —$CH_3$, or —$CH_2Ph$, and
wherein $R^2$ is —$CH_3$, —$C_4H_9$, -$nC_6H_{13}$, —$C_8H_{17}$, —$C_{16}H_{33}$, or —$CH_2Ph$. In one embodiment, $R^1$ is $C_4H_9$ and $R^2$ is $C_4H_9$.

Also disclosed are the synthesis of platinum(II) [Pt(II)] complexes containing N-heterocyclic carbene ligand (NHC) and BPI ligand, composition comprising platinum(II) [Pt (II)] complexes containing N-heterocyclic carbene ligand (NHC) and BPI ligand, methods of treating and preventing cancer or tumor in a subject, and a method of detecting the Pt(II) complex. Disclosed herein is a method of treating or preventing cancer/tumor comprising administering a pharmaceutical composition comprising at least one of the Pt(II)-NHC-BPI complexes in an effective amount for anticancer or anti-tumor activity. In certain embodiments, anticancer or anti-tumor activities includes, but are not limited to, the induction of cell death, inhibition of cellular proliferation, inhibition of angiogenesis, and inhibition of in vivo tumor growth. Provided herein is a method of detecting the Pt(II)-NHC-BPI complexes. In an embodiment, a signal is detected depending on fluorescence changes at proper wavelength. As provided herein, in one embodiment, Pt(II)-NHC-BPI complexes refer to a molecule of a platinum(II) ion connected to a N-heterocyclic carbene ligand and a BPI ligand. In one embodiment, platinum(II) [Pt(II)] complexes containing N-heterocyclic carbene ligand (NHC) is represented by structural formula I, derivatives thereof; or a pharmaceutically acceptable salt, solvate, or hydrate thereof.

As used herein, the phrase "acceptable salt," as used herein, includes salts formed from the charged Pt(II)-NHC-BPI complex and counter-anion(s).

As used herein, the phrase "counter-anion" refers to an ion associated with a positively charged Pt(II)-NHC-BPI complex. Non-limiting examples of counter-ions include halogens such as fluoride ($F^-$), chloride ($Cl^-$), bromide ($Br^-$), iodide ($I^-$); sulfate ($SO_4^{2-}$); phosphate ($PO_4^{3-}$); trifluoromethanesulfonate (triflate, $^-OTf$ or $CF_3SO_3^-$); acetate ($^-OAc$); nitrate ($NO_3^-$); perchlorate ($ClO_4^-$); hexafluorophosphate ($PF_6^-$) and hexafluoroacetylacetonate ($[CF_3C(O)CHC(O)CF_3]^-$).

In one embodiment, the invention relates to the synthesis of novel platinum(II) [Pt(II)] bearing N-heterocyclic carbene ligand and BPI ligand.

In another embodiment, the invention relates to a pharmaceutical composition for cancer treatment by inhibition of the proliferation of cancer cells in vitro comprising an effective amount of one or more of the Pt(II)-NHC-BPI complexes.

In another embodiment, the invention relates to a pharmaceutical composition for cancer treatment by the inhibition of tumor growth in vivo comprising an effective amount of one or more of the Pt(II)-NHC-BPI complexes.

In another embodiment, the invention relates to fluorescent detecting compounds, and the application in cellular imaging, comprising an effective amount of a Pt(II)-NHC-BPI complex.

The Pt(II)-NHC-BPI complexes of this invention can be represented by one or more of structural formula I, derivatives thereof; or a pharmaceutically acceptable salt, solvate, or hydrate thereof.

In one embodiment, the invention relates to a pharmaceutical composition for treating or preventing cancer/tumor. In certain embodiments, the treatment and prevention comprises induction of cell death, inhibition of cellular proliferation, inhibition of angiogenesis, and the inhibition of tumor growth in vivo. In one embodiment, the method comprises administering an effective amount of the Pt(II)-NHC-BPI complexes to a subject. In one embodiment, the method comprises detecting the Pt(II) complex is a subject comprising administering an effective amount of the Pt(II)-NHC-BPI complexes. In one embodiment, the Pt(II) complex is detected by fluorescence changes at proper wavelength. The Pt(II)-NHC-BPI complex has a formula I, derivatives thereof; or a pharmaceutically acceptable salt, solvate, or hydrate thereof,

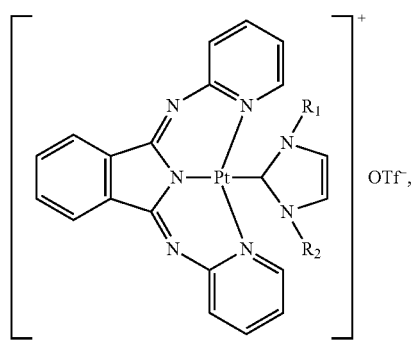

wherein $R^1$ is —$CH_3$, —$C_4H_9$, -$nC_6H_{13}$, —$CH_3$, or —$CH_2Ph$, and
wherein $R^2$ is —$CH_3$, —$C_4H_9$, -$nC_6H_{13}$, —$C_8H_{17}$, —$C_{16}H_{33}$, or —$CH_2Ph$.

5.2 Human Treatment 5.2.1 Formulations

The platinum(II) complexes provided herein can be administered to a patient in the conventional form of preparations, such as injections and suspensions. Suitable formulations can be prepared by methods commonly employed using conventional, organic or inorganic additives, such as an excipient selected from fillers or diluents, binders, disintegrants, lubricants, flavoring agents, preservatives, stabilizers, suspending agents, dispersing agents, surfactants, antioxidants or solubilizers.

Excipients that may be selected are known to those skilled in the art and include, but are not limited to fillers or diluents (e.g., sucrose, starch, mannitol, sorbitol, lactose, glucose, cellulose, talc, calcium phosphate or calcium carbonate and the like), a binder (e.g., cellulose, carboxymethylcellulose, methylcellulose, hydroxymethylcellulose, hydroxypropylmethylcellulose, polypropylpyrrolidone, polyvinylpyrrolidone, gelatin, gum arabic, polyethyleneglycol or starch and the like), a disintegrants (e.g., sodium starch glycolate, croscarmellose sodium and the like), a lubricant (e.g., magnesium stearate, light anhydrous silicic acid, talc or sodium lauryl sulfate and the like), a flavoring agent (e.g., citric acid, or menthol and the like), a preservative (e.g., sodium benzoate, sodium bisulfite, methylparaben or propylparaben and the like), a stabilizer (e.g., citric acid, sodium citrate or acetic acid and the like), a suspending agent (e.g., methylcellulose, polyvinyl pyrrolidone or aluminum stearate and the like), a dispersing agent (e.g., hydroxypropylmethylcellulose and the like), surfactants (e.g., sodium lauryl sulfate, polaxamer, polysorbates and the like), antioxidants (e.g., ethylene diamine tetraacetic acid (EDTA), butylated hydroxyl toluene (BHT) and the like) and solubilizers (e.g., polyethylene glycols, SOLUTOL®, GELUCIRE® and the like). The effective amount of the platinum(II) complexes provided herein in the pharmaceutical composition may be at a level that will exercise the desired effect.

In another embodiment, provided herein are compositions comprising an effective amount of platinum(II) complexes provided herein and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

Compositions can be formulated to contain a daily dose, or a convenient fraction of a daily dose, in a dosage unit. In general, the composition is prepared according to known methods in pharmaceutical chemistry. Capsules can be prepared by mixing the platinum(II) complexes provided herein with a suitable carrier or diluent and filling the proper amount of the mixture in capsules.

5.3 Method of Use

Solid tumor cancers that can be treated by the methods provided herein include, but are not limited to, sarcomas, carcinomas, and lymphomas. In specific embodiments, cancers that can be treated in accordance with the methods described include, but are not limited to, cancer of the breast, liver, neuroblastoma, head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

In particular embodiments, the methods for treating cancer provided herein inhibit, reduce, diminish, arrest, or stabilize a tumor associated with the cancer. In other embodiments, the methods for treating cancer provided herein inhibit, reduce, diminish, arrest, or stabilize the blood flow, metabolism, or edema in a tumor associated with the cancer or one or more symptoms thereof. In specific embodiments, the methods for treating cancer provided herein cause the regression of a tumor, tumor blood flow, tumor metabolism, or peritumor edema, and/or one or more symptoms associated with the cancer. In other embodiments, the methods for treating cancer provided herein maintain the size of the tumor so that it does not increase, or so that it increases by less than the increase of a tumor after administration of a standard therapy as measured by conventional methods available to one of skill in the art, such as digital rectal exam, ultrasound (e.g., transrectal ultrasound), CT Scan, MRI, dynamic contrast-enhanced MRI, or PET Scan. In specific embodiments, the methods for treating cancer provided herein decrease tumor size. In certain embodiments, the methods for treating cancer provided herein reduce the formation of a tumor. In certain embodiments, the methods for treating cancer provided herein eradicate, remove, or control primary, regional and/or metastatic tumors associated with the cancer. In some embodiments, the methods for treating cancer provided herein decrease the number or size of metastases associated with the cancer.

In certain embodiments, the methods for treating cancer provided herein reduce the tumor size (e.g., volume or diameter) in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor size (e.g., volume or diameter) prior to administration of platinum(II) complexes as assessed by methods well known in the art, e.g., CT Scan, MRI, DCE-MRI, or PET Scan. In particular embodiments, the methods for treating cancer provided herein reduce the tumor volume or tumor size (e.g., diameter) in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor size (e.g., diameter) in a subject prior to administration of platinum(II) complexes as assessed by methods well known in the art, e.g., CT Scan, MRI, DCE-MRI, or PET Scan.

In certain embodiments, the methods for treating cancer provided herein reduce the tumor perfusion in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor perfusion prior to administration of platinum(II) complexes as assessed by methods well known in the art, e.g., MRI, DCE-MRI, or PET Scan. In particular embodiments, the methods for treating cancer provided herein reduce the tumor perfusion in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor perfusion prior to administration of platinum(II) complexes, as assessed by methods well known in the art, e.g., MRI, DCE-MRI, or PET Scan.

In particular aspects, the methods for treating cancer provided herein inhibit or decrease tumor metabolism in a subject as assessed by methods well known in the art, e.g., PET scanning. In specific embodiments, the methods for treating cancer provided herein inhibit or decrease tumor metabolism in a subject by at least about 5%, 10%, 15%, 20%, 25%, 30%, 35%, 40%, 45%, 50%, 55%, 60%, 65%, 80%, 85%, 90%, 95%, or 100%, relative to tumor metabolism prior to administration of platinum(II) complexes, as assessed by methods well known in the art, e.g., PET scanning. In particular embodiments, the methods for treating cancer provided herein inhibit or decrease tumor metabolism in a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor metabolism prior to administration of platinum(II) complexes, as assessed by methods well known in the art, e.g., PET scan.

5.4 Patient Population

In some embodiments, a subject treated for cancer in accordance with the methods provided herein is a human who has or is diagnosed with cancer. In other embodiments, a subject treated for cancer in accordance with the methods provided herein is a human predisposed or susceptible to cancer. In some embodiments, a subject treated for cancer in accordance with the methods provided herein is a human at risk of developing cancer.

In one embodiment, a subject treated for cancer in accordance with the methods provided herein is a human infant. In another embodiment, a subject treated for cancer in accordance with the methods provided herein is a human toddler. In another embodiment, a subject treated for cancer in accordance with the methods provided herein is a human child. In another embodiment, a subject treated for cancer in accordance with the methods provided herein is a human adult. In another embodiment, a subject treated for cancer in accordance with the methods provided herein is a middle-aged human. In another embodiment, a subject treated for cancer in accordance with the methods provided herein is an elderly human.

In certain embodiments, a subject treated for cancer in accordance with the methods provided herein has a cancer that metastasized to other areas of the body, such as the bones, lung and liver. In certain embodiments, a subject treated for cancer in accordance with the methods provided herein is in remission from the cancer. In some embodiments, a subject treated for cancer in accordance with the methods provided herein that has a recurrence of the cancer. In certain embodiments, a subject treated in accordance with the methods provided herein is experiencing recurrence of one or more tumors associated with cancer.

In certain embodiments, a subject treated for cancer in accordance with the methods provided herein is a human that is about 1 to about 5 years old, about 5 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between. In a specific embodiment, a subject treated for cancer in accordance with the methods provided herein is a human that is 18 years old or older. In a particular embodiment, a subject treated for cancer in accordance with the methods provided herein is a human child that is between the age of 1 year old to 18 years old. In a certain embodiment, a subject treated for cancer in accordance with the methods provided herein is a human that is between the age of 12 years old and 18 years old. In a certain embodiment, the subject is a male human. In another embodiment, the subject is a female human. In one embodiment, the subject is a female human that is not pregnant or is not breastfeeding. In one embodiment, the subject is a female that is pregnant or will/might become pregnant, or is breast feeding.

In some embodiments, a subject treated for cancer in accordance with the methods provided herein is administered platinum(II) complexes or a pharmaceutical composition thereof, or a combination therapy before any adverse effects or intolerance to therapies other than the platinum(II) complexes develops. In some embodiments, a subject treated for cancer in accordance with the methods provided herein is a refractory patient. In a certain embodiment, a refractory patient is a patient refractory to a standard therapy (e.g., surgery, radiation, anti-androgen therapy and/or drug therapy such as chemotherapy). In certain embodiments, a patient with cancer is refractory to a therapy when the cancer has not significantly been eradicated and/or the one or more symptoms have not been significantly alleviated. The determination of whether a patient is refractory can be made either in vivo or in vitro by any method known in the art for assaying the effectiveness of a treatment of cancer, using art-accepted meanings of "refractory" in such a context. In various embodiments, a patient with cancer is refractory when one or more tumors associated with cancer, have not decreased or have increased. In various embodiments, a patient with cancer is refractory when one or more tumors metastasize and/or spread to another organ.

In some embodiments, a subject treated for cancer accordance with the methods provided herein is a human that has proven refractory to therapies other than treatment with platinum(II) complexes, but is no longer on these therapies. In certain embodiments, a subject treated for cancer in accordance with the methods provided herein is a human already receiving one or more conventional anti-cancer therapies, such as surgery, drug therapy such as chemotherapy, anti-androgen therapy or radiation. Among these patients are refractory patients, patients who are too young for conventional therapies, and patients with recurring tumors despite treatment with existing therapies.

5.5 Dosage

In one aspect, a method for treating cancer presented herein involves the administration of a unit dosage of platinum(II) complexes or a pharmaceutical composition thereof. The dosage may be administered as often as determined effective (e.g., once, twice or three times per day, every other day, once or twice per week, biweekly or monthly). In certain embodiments, a method for treating cancer presented herein involves the administration to a subject in need thereof of a unit dose of platinum(II) complexes that can be determined by one skilled in the art.

In some embodiments, a unit dose of platinum(II) complexes or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly, and the dosage may be administered orally.

5.6 Combination Therapy

Presented herein are combination therapies for the treatment of cancer which involve the administration of platinum (II) complexes in combination with one or more additional therapies to a subject in need thereof. In a specific embodiment, presented herein are combination therapies for the treatment of cancer which involve the administration of an effective amount of platinum(II) complexes in combination with an effective amount of another therapy to a subject in need thereof.

As used herein, the term "in combination," refers, in the context of the administration of platinum(II) complexes, to the administration of platinum(II) complexes prior to, concurrently with, or subsequent to the administration of one or more additional therapies (e.g., agents, surgery, or radiation) for use in treating cancer. The use of the term "in combination" does not restrict the order in which platinum(II) complexes and one or more additional therapies are administered to a subject. In specific embodiments, the interval of time between the administration of platinum(II) complexes and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, platinum(II) complexes and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the combination therapies provided herein involve administering platinum(II) complexes daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain embodiments, platinum(II) complexes and one or more additional therapies are cyclically administered to a subject. Cycling therapy involves the administration of platinum(II) complexes for a period of time, followed by the administration of one or more additional therapies for a period of time, and repeating this sequential administration. In certain embodiments, cycling therapy may also include a period of rest where platinum(II) complexes or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an embodiment, the number of cycles administered is from 1 to 12 cycles, from 2 to 10 cycles, or from 2 to 8 cycles.

In some embodiments, the methods for treating cancer provided herein comprise administering platinum(II) complexes as a single agent for a period of time prior to administering the platinum(II) complexes in combination with an additional therapy. In certain embodiments, the methods for treating cancer provided herein comprise administering an additional therapy alone for a period of time prior to administering platinum(II) complexes in combination with the additional therapy.

In some embodiments, the administration of platinum(II) complexes and one or more additional therapies in accordance with the methods presented herein have an additive effect relative the administration of platinum(II) complexes or said one or more additional therapies alone. In some embodiments, the administration of platinum(II) complexes and one or more additional therapies in accordance with the methods presented herein have a synergistic effect relative to the administration of the Compound or said one or more additional therapies alone.

As used herein, the term "synergistic," refers to the effect of the administration of platinum(II) complexes in combination with one or more additional therapies (e.g., agents), which combination is more effective than the additive effects of any two or more single therapies (e.g., agents). In a specific embodiment, a synergistic effect of a combination therapy permits the use of lower dosages (e.g., sub-optimal doses) of platinum(II) complexes or an additional therapy and/or less frequent administration of platinum(II) complexes or an additional therapy to a subject. In certain embodiments, the ability to utilize lower dosages of platinum(II) complexes or of an additional therapy and/or to administer platinum(II) complexes or said additional therapy less frequently reduces the toxicity associated with the administration of platinum(II) complexes or of said additional therapy, respectively, to a subject without reducing the efficacy of platinum(II) complexes or of said additional therapy, respectively, in the treatment of cancer. In some embodiments, a synergistic effect results in improved efficacy of platinum(II) complexes and each of said additional therapies in treating cancer. In some embodiments, a synergistic effect of a combination of platinum(II) complexes and one or more additional therapies avoids or reduces adverse or unwanted side effects associated with the use of any single therapy.

The combination of platinum(II) complexes and one or more additional therapies can be administered to a subject in the same pharmaceutical composition. Alternatively, platinum(II) complexes and one or more additional therapies can be administered concurrently to a subject in separate pharmaceutical compositions. Platinum(II) complexes and one or more additional therapies can be administered sequentially to a subject in separate pharmaceutical compositions. Platinum(II) complexes and one or more additional therapies may also be administered to a subject by the same or different routes of administration.

The combination therapies provided herein involve administering to a subject to in need thereof platinum(II) complexes in combination with conventional, or known, therapies for treating cancer. Other therapies for cancer or a condition associated therewith are aimed at controlling or relieving one or more symptoms. Accordingly, in some embodiments, the combination therapies provided herein involve administering to a subject to in need thereof a pain reliever, or other therapies aimed at alleviating or controlling one or more symptoms associated with or a condition associated therewith.

Specific examples of anti-cancer agents that may be used in combination with platinum(II) complexes include: a hormonal agent (e.g., aromatase inhibitor, selective estrogen receptor modulator (SERM), and estrogen receptor antagonist), chemotherapeutic agent (e.g., microtubule dissembly blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with platinum(II) complexes include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with platinum(II) complexes include microtubule disassembly blocker, antimetabolite, topisomerase inhibitor, and DNA crosslinker or damaging agent. Chemotherapeutic agents that are microtubule disassembly blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®)).

Chemotherapeutic agents that are antimetabolites include, but are not limited to, folate anitmetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capcitabine, gemcitabine (GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of other therapies that may be administered to a subject in combination with platinum(II) complexes include:

(1) a statin such as lovostatin (e.g., branded/marketed as MEVACOR®);

(2) an mTOR inhibitor such as sirolimus which is also known as Rapamycin (e.g., branded/marketed as RAPAMUNE®), temsirolimus (e.g., branded/marketed as TORISEL®), evorolimus (e.g., branded/marketed as AFINITOR®), and deforolimus;

(3) a farnesyltransferase inhibitor agent such as tipifarnib;

(4) an antifibrotic agent such as pirfenidone;

(5) a pegylated interferon such as PEG-interferon alfa-2b;

(6) a CNS stimulant such as methylphenidate (branded/marketed as RITALIN®);

(7) a HER-2 antagonist such as anti-HER-2 antibody (e.g., trastuzumab) and kinase inhibitor (e.g., lapatinib);

(8) an IGF-1 antagonist such as an anti-IGF-1 antibody (e.g., AVE1642 and IMC-A 1) or an IGF-1 kinase inhibitor;

(9) EGFR/HER-1 antagonist such as an anti-EGFR antibody (e.g., cetuximab, panitumamab) or EGFR kinase inhibitor (e.g., erlotinib; gefitinib);

(10) SRC antagonist such as bosutinib;

(11) cyclin dependent kinase (CDK) inhibitor such as seliciclib;

(12) Janus kinase 2 inhibitor such as lestaurtinib;

(13) proteasome inhibitor such as bortezomib;

(14) phosphodiesterase inhibitor such as anagrelide;

(15) inosine monophosphate dehydrogenase inhibitor such as tiazofurine;

(16) lipoxygenase inhibitor such as masoprocol;

(17) endothelin antagonist;

(18) retinoid receptor antagonist such as tretinoin or alitretinoin;

(19) immune modulator such as lenalidomide, pomalidomide, or thalidomide;

(20) kinase (e.g., tyrosine kinase) inhibitor such as imatinib, dasatinib, erlotinib, nilotinib, gefitinib, sorafenib, sunitinib, lapatinib, or TG100801;

(21) non-steroidal anti-inflammatory agent such as celecoxib (branded/marketed as CELEBREX®);

(22) human granulocyte colony-stimulating factor (G-CSF) such as filgrastim (branded/marketed as NEUPOGEN®);

(23) folinic acid or leucovorin calcium;

(24) integrin antagonist such as an integrin α5β1-antagonist (e.g., JSM6427);

(25) nuclear factor kappa beta (NF-κβ) antagonist such as OT-551, which is also an anti-oxidant;

(26) hedgehog inhibitor such as CUR61414, cyclopamine, GDC-0449, and anti-hedgehog antibody;

(27) histone deacetylase (HDAC) inhibitor such as SAHA (also known as vorinostat (branded/marketed as ZOLINZA)), PCI-24781, SB939, CHR-3996, CRA-024781, ITF2357, JNJ-26481585, or PCI-24781;

(28) retinoid such as isotretinoin (e.g., branded/marketed as ACCUTANE®);

(29) hepatocyte growth factor/scatter factor (HGF/SF) antagonist such as HGF/SF monoclonal antibody (e.g., AMG 102);

(30) synthetic chemical such as antineoplaston;

(31) anti-diabetic such as rosaiglitazone (e.g., branded/marketed as AVANDIA®);

(32) antimalarial and amebicidal drug such as chloroquine (e.g., branded/marketed as ARALEN®);

(33) synthetic bradykinin such as RMP-7;

(34) platelet-derived growth factor receptor inhibitor such as SU-101;

(35) receptor tyrosine kinase inhibitorsof Flk-1/KDR/VEGFR2, FGFR1 and PDGFR beta such as SU5416 and SU6668;

(36) anti-inflammatory agent such as sulfasalazine (e.g., branded/marketed as AZULFIDINE®); and

(37) TGF-beta antisense therapy.

6 EXAMPLES

Example 6.1: Preparation and Characterization of the NHC Complexes

The following examples illustrate the synthesis and characterization of the platinum(II) complexes.

[Pt(BPI)(NHC)](OTf) with different alkyl chains and aromatic groups on the NHC ligands were prepared by refluxing [Pt(BPI)Cl][25] with corresponding imidazolium salt in the presence of base (FIG. 1; See Supporting Information for experimental details and characterization data). The structure of 1a was further examined by X-ray crystallography (FIG. 2 and Table 1) and the NHC ligand was found to be perpendicular to the plane of BPI ligand with bond angle (C19-Pt1-N5) of 90.6°.

TABLE 1

Crystal data and structure refinement data for 1a.

| | |
|---|---|
| Identification code | 1a |
| Empirical formula | $C_{23}H_{20}N_7Pt \cdot CF_3O_3S$* |
| Formula weight | 738.62 |
| Temperature/K | 100 |
| Crystal system | monoclinic |
| Space group | C2/c |
| a/Å | 24.5594 (9) |
| b/Å | 14.9575 (6) |
| c/Å | 15.7468 (6) |
| α/° | 90.00 |
| β/° | 119.678 (1)° |
| γ/° | 90.00 |
| Volume/Å$^3$ | 5025.7 (3) |
| Z | 8 |
| $\rho_{calc}$ g/cm$^3$ | 1.515 |
| μ/mm$^{-1}$ | 11.80 |
| F(000) | 2864.0 |
| Crystal size/mm$^3$ | 0.06 × 0.02 × 0.02 |
| Radiation | CuKα (λ = 1.54178) |
| 2Θ range for data collection/° | 3.60 to 66.7 |
| Index ranges | −29 ≤ h ≤ 28, −14 ≤ k ≤ 17, −18 ≤ l ≤ 18 |
| Reflection collected | 4152 |
| Independent reflections | 4152 [$R_{int}$ = 0.083] |
| Data/restraints/parameters | 4390/11/380 |
| Goodness-of-fit of F$^2$ | 1.07 |
| Final R indexes [I >= 2σ (I)] | $R_1$ = 0.054, $wR_2$ = 0.148 |
| Largest diff. peak/hole/eÅ$^{-3}$ | 1.37/−1.25 |

*Satisfactory disorder models for the solvent and another triflic

The UV-visible absorption data and spectra of 1a-1j were depicted in Table 2 and FIG. 3(A). The absorption spectra of $CH_2Cl_2$ solutions of 1b, 1i and 1j showed intense absorptions at 400-550 nm, arising primarily from π→π* (L) intraligand (IL) and 5d (Pt)→π* (L) metal-to-ligand charge transfer (MLCT) transitions.[25] Upon photoexcitation, 1b, 1i and 1j in degassed $CH_2Cl_2$ displayed vibronic structured emission spectra with emission maxima at 588 nm (φ=0.027, τ=5.3 μs), 627 nm (φ=0.005, τ=1.1 μs) and 566 nm (φ=0.12, τ=10.9 μs), respectively (FIG. 3(B)). The alkyl chain length of the NHC ligands was found to not affect photophysical properties of the complexes significantly (Tables 2 and 3).

TABLE 2

UV-visible absorption data of 1a-1j ($2 \times 10^{-5}$ mol $dm^{-1}$ in $CH_2Cl_2$)

| Complex | $\lambda_{abs}$/nm ($\varepsilon$/$dm^3mol^{-1}cm^{-1}$) |
|---|---|
| 1a | 247 (49186), 275 (24960), 343 (25141), 370 (11450), 408 (8265), 434 (17922), 461 (22286) |
| 1b | 247 (36940), 276 (18928), 344 (19119), 372 (9195), 406 (6510), 434 (13736), 462 (16941) |
| 1c | 247 (41946), 277 (21053), 344 (21986), 370 (10352), 408 (7396), 434 (15708), 462 (19576) |
| 1d | 247 (51933), 276 (26519), 344 (27180), 370 (12741), 408 (9239), 434 (19590), 462 (24388) |
| 1e | 247 (47280), 276 (24119), 344 (24650), 370 (11414), 408 (8207), 434 (17658), 462 (22041) |
| 1f | 247 (47522), 273 (23426), 343 (24338), 370 (11373), 408 (8365), 434 (17422), 462 (21681) |
| 1g | 247 (45308), 275 (21894), 344 (23816), 370 (11515), 408 (8674), 434 (17518), 462 (21396) |
| 1h | 248 (67601), 331 (20472), 346 (22531), 435 (14407), 459(15491) |
| 1i | 248 (42466), 277 (27255), 345 (16922), 386 (9580), 481 (10084) |
| 1j | 286 (53202), 297 (55807), 346 (21484), 405 (32808), 421 (36269), 450 (31028) |

TABLE 3

Summary of emission data.

| | $\lambda_{max}$ (nm) | Photoluminescence quantum yield ($\Phi$) | Lifetime ($\tau$; $\mu$s) |
|---|---|---|---|
| 1a | 588 | 0.029 | 5.5 |
| 1b | 588 | 0.027 | 5.3 |
| 1c | 588 | 0.028 | 5.0 |
| d | 588 | 0.03 | 5.9 |
| 1e | 588 | 0.029 | 5.9 |
| 1f | 588 | 0.023 | 5.7 |
| 1g | 588 | 0.024 | 5.1 |
| 1h | 630 | 0.001 | 0.4 |
| 1i | 627 | 0.005 | 1.1 |
| 1j | 566 | 0.12 | 10.9 |

As compared with the chloro-precursor complex [Pt(BPI)Cl] (1i), both the absorption and emission spectra of platinum(II) complexes with NHC ligands (1b and 1j) displayed distinct blue-shifts (FIG. 3). With reference to previous spectroscopic work on related platinum(II) complexes,[26] the observed blue-shifts in [Pt(BPI)(NHC)]$^+$ were probably attributed to an enhanced contribution from the $^3$IL state and a reduced $^3$MLCT character. On the other hand, 1j, which has an extended $\pi$-conjugation through benzannulation of the pincer ligand, showed blue-shift in both the absorption and emission spectra, as compared to that of 1f (Table 2 and 3). This can be rationalized by destabilization of the LUMO with successive expansion of the $\pi$-system of the pyrrolate moieties, as supported by similar finding reported previously.[27]

Interestingly, in one embodiment, proteomics data and in vitro biochemical assays at sub-cytotoxic concentrations reveal that a representative complex, 1b, can regulate uPA/uPAR-mediated and VEGF-induced angiogenic pathways. Ex vivo anti-angiogenic properties of 1b is further demonstrated by chorioallantoic membrane (CAM) assay. More importantly, treatment of nude mice bearing highly metastatic MDA-MB231 xenograft by 1b show significant reduction in tumor volume. Immunohistochemical analysis of tumor tissues from treated mice supports the promising in vivo antitumor as well as anti-angiogenic activities of 1b, while blood biochemistry reveal minimal systemic toxicity found in the treated mice. All of these results indicate that these dual cytotoxic and anti-angiogenic platinum(II) complexes are useful for treating cancer, including non-curable highly metastatic cancer.

The luminescence properties of [Pt(BPI)(NHC)]$^+$ in live cells were also examined. After treating human cervical epithelial carcinoma (HeLa) cells with 1b (5 $\mu$M) for 15 min, a strong green luminescence was observed from cytoplasm of the cells (FIG. 4(A)), demonstrating the readiness of monitoring cellular uptake and localization of 1b by its strong luminescence in vitro. The exact subcellular location of 1b was investigated by co-staining with organelle-specific probes. It was noted that 1b specifically localized in ER, as supported by high Pearson's correlation coefficient for co-localization between 1b and ER-Tracker™ (0.83; FIG. 4(A)). Control experiment showed that there was no background signal in the rhodamine and FITC channel when the cells were treated by 1b and ER-Tracker™ respectively (FIG. 5). In addition, no significant co-localization between 1b and mitochondria-specific Mitotracker® or lysosome-specific Lysotracker® was observed (Pearson's correlation coefficient=0.45 and 0.55 respectively; FIG. 6), indicating that 1b was preferentially accumulated in ER of HeLa cells In view of the enormous success of platinum(II) compounds for anti-cancer treatment,[28] in vitro cytotoxicity of [Pt(BPI)(NHC)]$^+$ towards various cancer cell lines including HeLa, colon carcinoma (HCT116), lung cancer (NCI-H460) and highly invasive triple-negative breast cancer (MDA-MB-231), as well as non-tumorigenic immortalized human hepatocyte (MIHA) were examined. 1a-1h were cytotoxic against the cancer cells with IC$_{50}$ (dose required to inhibit 50% of cellular growth) ranging from 0.14±0.01 to 18.21±1.52 $\mu$M after 72 h treatment. They were found to be more potent in killing most of the cancer cells investigated than cisplatin (11.75±1.36 to 77.19±7.82 $\mu$M). Among these platinum(II) complexes, 1b displayed relatively higher cytotoxicity towards NCI-H460 and HCT116 cells than that towards non-tumorigenic MIHA cells (16- and 19-fold difference in IC$_{50}$ values respectively; Table 4), suggesting its selectivity on killing cancer cells over non-tumorigenic cells. As a result, 1b was selected as a target compound and its anti-cancer properties were further investigated.

TABLE 4

In vitro cytotoxicity of 1a-1h against human cell lines of HeLa, NCI-H460, HCT116, MDA-MB-231 and MiHa. The IC$_{50}$ ($\mu$M) was determined by MTT assay pon incubation of the live cells with the complexes for 72 h.

| | HeLa | NCI-H460 | HCT116 | MDA-MB-231 | MiHa |
|---|---|---|---|---|---|
| 1a | 5.45 ± 0.52 | 2.72 ± 0.56 | 1.19 ± 0.06 | 6.39 ± 0.53 | 7.32 ± 3.65 |
| 1b | 1.63 ± 0.85 | 0.28 ± 0.18 | 0.23 ± 0.02 | 2.34 ± 0.19 | 4.46 ± 0.97 |
| 1c | 1.56 ± 0.28 | 0.16 ± 0.14 | 0.14 ± 0.01 | 1.62 ± 0.16 | 0.27 ± 0.11 |
| 1d | 3.25 ± 0.43 | 1.16 ± 0.11 | 0.39 ± 0.06 | 4.44 ± 0.15 | 1.04 ± 0.59 |
| 1e | 2.05 ± 0.49 | 2.25 ± 0.06 | 2.87 ± 0.41 | 7.45 ± 0.50 | 3.77 ± 1.16 |
| 1f | 2.23 ± 0.29 | 1.68 ± 0.33 | 0.49 ± 0.10 | 3.78 ± 0.48 | 1.97 ± 1.06 |
| 1g | 3.43 ± 0.22 | 0.90 ± 0.06 | 1.55 ± 0.38 | 4.15 ± 1.03 | 2.13 ± 0.96 |
| 1h | 14.63 ± 1.32 | 13.2 ± 1.23 | 7.46 ± 0.97 | 18.21 ± 1.52 | 27.46 ± 12.80 |
| Cisplatin | 12.90 ± 3.84 | 24.9 ± 3.19 | 11.75 ± 1.36 | 77.19 ± 7.82 | >100 |

Since 1b was found to accumulate in ER domain as revealed by confocal fluorescence microscopy images (FIG. 4(A)), this prompted us to investigate any ER stress induced by 1b that accounted for its high cytotoxicity towards cancer cells. Western blotting analysis showed a significant up-regulation of phosphorylated RNA-dependent protein kinase-like endoplasmic reticulum kinase (PERK) upon treatment of MDA-MB-231 cells with 1b (5 uM) for 6, 12, 24 and 48 h (FIG. 4(B)). Also, phosphorylated eukaryotic initiation factor 2a (eIF2α) and C/EBP homologous protein (CHOP) were also found to be stimulated under same conditions, suggesting that 1b could induce ER stress.[29,30]

In addition to ER stress, apoptosis-related protein such as poly(ADP-ribose) polymerase (PARP) and caspases 3 and 9 were cleaved in MDA-MB-231 cells treated with 1b for 48 h (FIG. 4(C)), indicative of cell apoptosis. Cell cycle analysis of MDA-MB-231 cells treated with 1b for 24 h revealed a marked accumulation in the G0/G1 phase from 36.4% to 64% (FIG. 7(B)). The G0/G1 cell-cycle arrest was associated with stimulation of p15 expression and down-regulation of cyclin D1/D3 and CDK 4/6, as indicated by western blot analysis (FIG. 7(C)). In addition, there was dose-dependent increase (up to 8-fold) of cell population in sub-G1 phase (FIG. 7(A)), and this was a hallmark of apoptosis owing to DNA fragmentation. On the other hand, JC1 staining[31] of cells treated with 1b showed a decrease in ratios of orange to green fluorescence (1580/1530) with increasing dosage of 1b (FIGS. 8(A)-(D)). This indicated that 1b could induce mitochondria dysfunction. Collectively, in vitro assays confirm that 1b at its cytotoxic concentrations could induce ER stress, nuclear fragmentation and mitochondria dysfunction, leading to subsequent apoptotic events.

To obtain a holistic insight into the mechanism of action of 1b, proteomic analysis on 1b-treated MDA-MB-231 cells was performed using HPLC-LTQ-Orbitrap MS. A bioinformatics analysis of the proteomic data showed that CHIP (c-terminal Hsp70-interacting protein), c-Kit and Von Hippel-Lindau (VHL) protein pathway were one of the most predominantly modulated pathways in MDA-MB-231 cells treated with 1b (5 µM) for 5 h with high statistical significance (Table 5). Interestingly, these three pathways were related to angiogenic responses of cancer cells. The expression level of CHIP is negatively correlated with VEGFR2 which is an important receptor for initiation of angiogenesis;[32] Von Hippel-Lindau (VHL) protein is capable of suppressing tumor growth through down-regulation of a number of angiogenic factors;[33] c-kit receptor regulate angiogenesis by PI3K/Akt downstream signaling pathway.[34]

In view of the regulation of angiogenesis-related pathways by 1b as identified by proteomic data, anti-angiogenic and anti-metastatic properties of 1b were evaluated. Wound closure assays showed that 1b effectively inhibited migration of MDA-MB-231 cells at sub-cytotoxic concentrations (0.25-1 µM) after a 24 h treatment in a concentration- and time-dependent manner (FIGS. 9(A) and 9(B), and 10); this effect was not due to the cytotoxicity of 1b as the cells were found to have insignificant growth inhibition under these concentrations of 1b (FIG. 11). On the other hand, transwell invasive assays revealed significant inhibition of invasion of MDA-MB-231 cells by 1b at its sub-cytotoxic concentrations after 24 h treatment (FIGS. 9(C) and (D)). In tube formation assay, 1b displayed significant inhibition on the angiogenesis of MS1 cells, as indicated by the loss of ability of the endothelial cells to form three-dimensional tube-like structures after treatment with 1b for 3 h at sub-cytotoxic concentrations (>90% cells remained viable; FIGS. 12(A)-(B)). All these data suggest that 1b not only can induce apoptosis and cell cycle arrest at its cytotoxic concentrations, but also can inhibit metastasis of highly invasive MDA-MB-231 at its sub-cytotoxic concentrations.

TABLE 5

The seven signaling pathways showing highest −log(p-value) in proteomic analysis of MDA-MB-231 cells treated with 1b (5 µM).

| Pathways | Score | p-value |
| --- | --- | --- |
| HIF-1alpha pathway | 9.17 | 7.12E−05 |
| TGF beta pathway | 9.00 | 1.06E−04 |
| CHIP--/Pael-R | 8.71 | 2.08E−04 |
| c-Kit pathway | 8.22 | 6.42E−04 |
| RSK1 --> MITF{pSer}{ub} | 7.99 | 1.08E−03 |
| VHL --> HIF-1alphadegradation | 7.92 | 1.26E−03 |
| Plk1cellcycleregulation | 7.73 | 1.97E−03 |

Figures 13A, 13B:
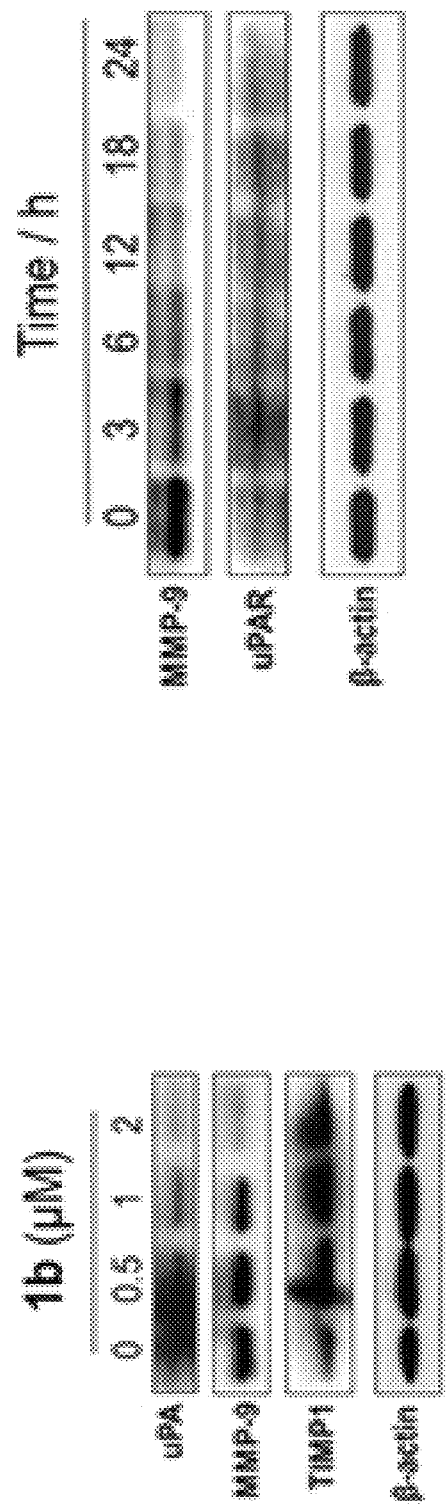
Figure 13D:
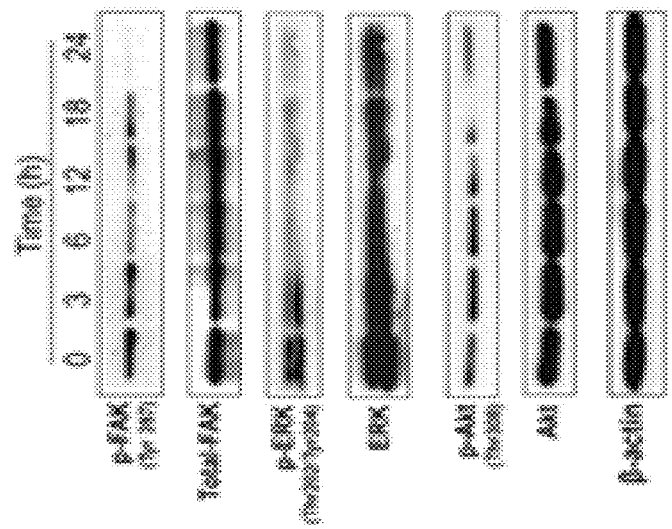

To gain better insight into the anti-angiogenic properties of 1b, effects of 1b on uPA/uPAR system were first investigated, as this system has been found to play crucial roles in growth, metastasis and angiogenesis of many solid malignancies, e.g. by activation of MMPs for ECM degradation and triggering downstream intracellular signaling for metastasis.[10,35] Western blotting experiments showed that the expression level of uPA and MMP-9 (examples of MMPs) decreased significantly when MDA-MB-231 cells were treated with increasing concentration of 1b (FIG. 13(A)) or increasing incubation time of 1b (FIG. 13(B)). In contrast, the expression of TIMP-1, a tissue inhibitor of MMPs,[36] moderately increased after treatment with 1b (FIG. 13(A)). These results suggests that 1b could slow down uPA/uPAR-mediated ECM proteolysis process, thus inhibiting tumor progression.

Figure 13C:
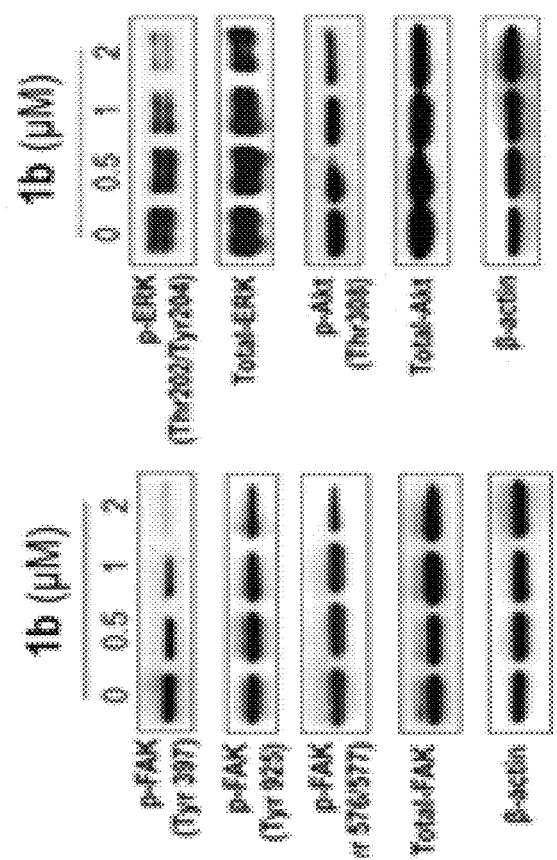
Figure 14B:
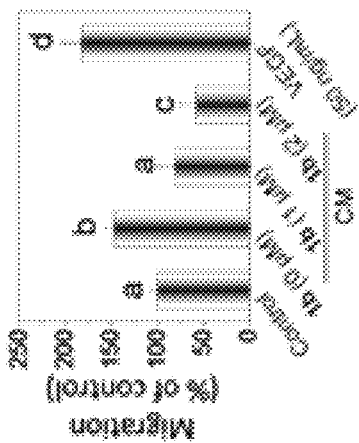
Figure 14C:
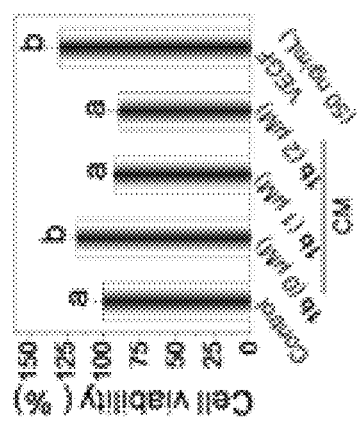
Figure 14A:
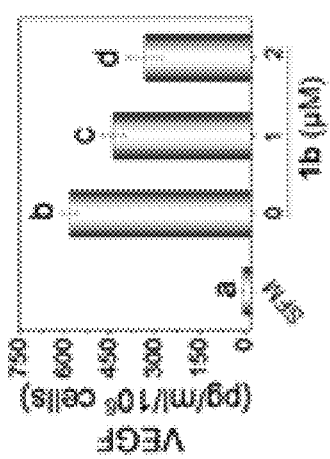
Figure 14D:
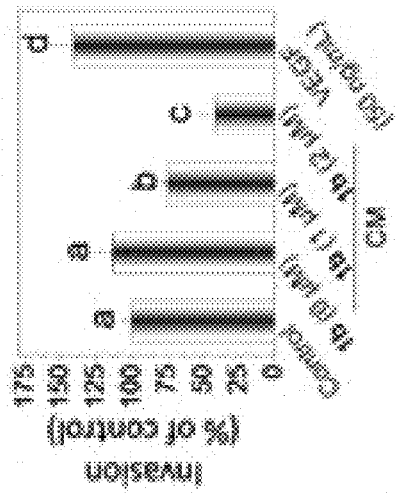
Figure 14E:
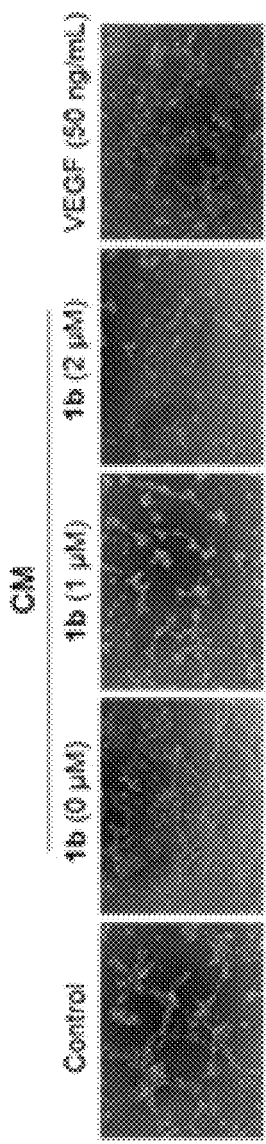
Figure 14F:
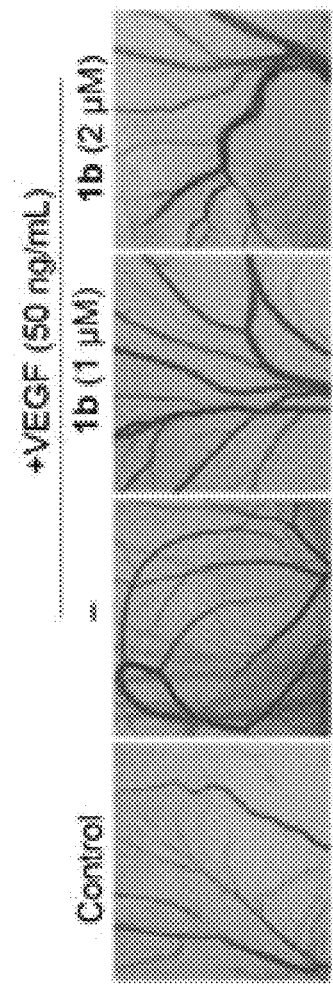

In addition to the regulation of proteolysis, 1b was found to significantly suppress phosphorylation of focal adhesion kinase (FAK) at the site of Tyr397, and moderately inhibited levels of phosphorylation of FAK at Tyr925 and Tyr576/577, while exhibited little effect on total protein level of FAK (FIGS. 13(C) and (D)). Moreover, 1b significantly inhibited phosphorylation of ERK and Akt in a dose- and time-dependent manner (FIGS. 13(C) and (D)). PI3K/Akt[37] and Ras/MEK/ERK[38] protein kinase pathways have been reported to be downstream signaling pathways after stimulation of FAK upon formation of integrin and uPAR complex, and these pathways can facilitate cell invasion and proliferation. Notably, PI3K/Akt pathway is also the downstream signaling pathway of c-kit receptor which was identified as one of the predominantly modulated pathways in proteomic studies of MDA-MB-231 cells treated with 1b.

The effects of 1b, LY294002 (PI3K inhibitor)[39] and U0126 (ERK inhibitor)[40] on PI3K and ERK signaling pathways were further investigated. LY294002, U0126 or 1b alone displayed insignificant cell growth inhibitory effects (1b is at sub-cytotoxic concentration; FIG. 13(E)), but notable inhibition on the migration and invasion of MDA-MB-231 cells (FIGS. 13(F) and (G)). Co-treatment of MDA-MB-231 cells with 1b, and LY294002 or U0126, was found to inhibit cell growth, migration and invasion significantly (FIGS. 13(E), (F) and (G)). All these data indicate the anti-angiogenic properties of 1b by inhibiting uPA/uPAR-mediated ECM proteolysis and downstream intracellular signaling for metastasis.

Vascular endothelial growth factor (VEGF) is another critical mediator of angiogenesis and regulates most of the steps in angiogenic cascade, including proliferation, migration and tube formation of endothelial cells.[41,42] Previous studies demonstrated that MMP-9 and uPA were able to facilitate degradation of ECM, leading to release or activation of VEGF, thus promoting tumor growth and angiogenesis.[43-45] Therefore, effect of 1b on secretion level of VEGF in the culture media of MDA-MB-231 cells was investigated by Quantikine® ELISA kit. It was found that VEGF secretion level was reduced by 50% upon treating MDA-MB-231 cells with 1b for 24 h, as compared to the untreated cells (FIG. 14(A)).

To further validate anti-angiogenic properties of 1b, effects of 1b on another aggressive cell line, human umbilical vein endothelial cell (HUVEC) line, were studied. HUVEC is a well-established cell line for studying angiogenesis.[46] It was found that exposure of HUVECs to VEGF (50 ng/mL) lead to promoted cell growth, migration, invasion and tube formation (FIGS. 14(B)-(D)). In order to mimic the tumor microenvironment in vitro, the conditioned media (CM) of MDA-MB-231 cells containing VEGF (13.4 ng/mL) was collected for incubation of HUVECs. As shown in FIGS. 14(B)-14(E), 1b significantly suppressed CM-mediated migration, invasion and tube formation of HUVECs at sub-cytotoxic concentrations. More interestingly, chorioallantoic membrane (CAM) assay[43] showed effective ex vivo anti-angiogenic properties of 1b (FIG. 14(F)). Taken together, these results demonstrate that 1b not only can inhibit VEGF secretion from tumor cells, but also suppress VEGF-mediated angiogenesis.

Figure 15B:
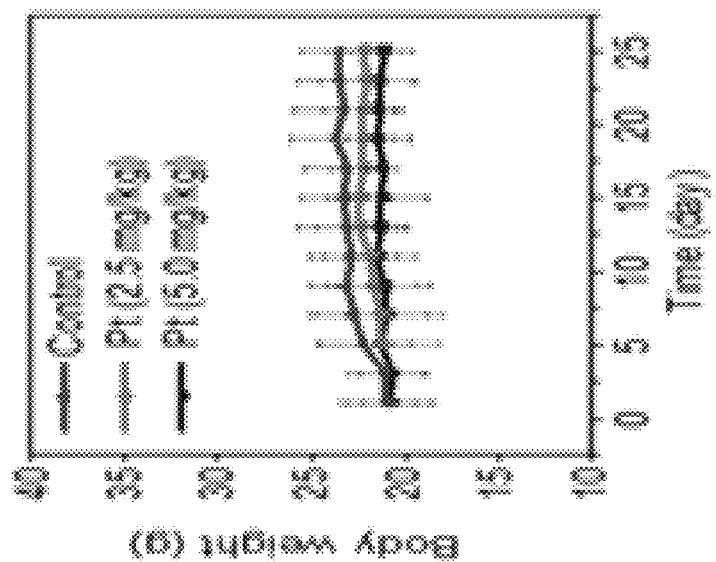
Figure 15A:
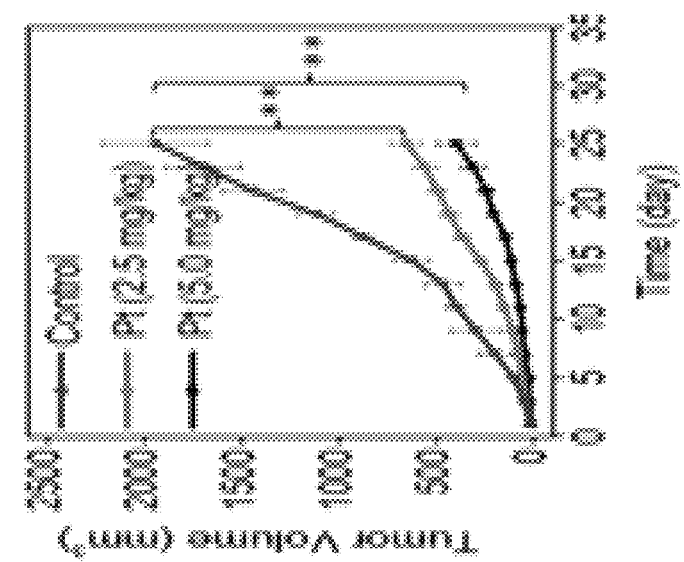
Figure 15C:
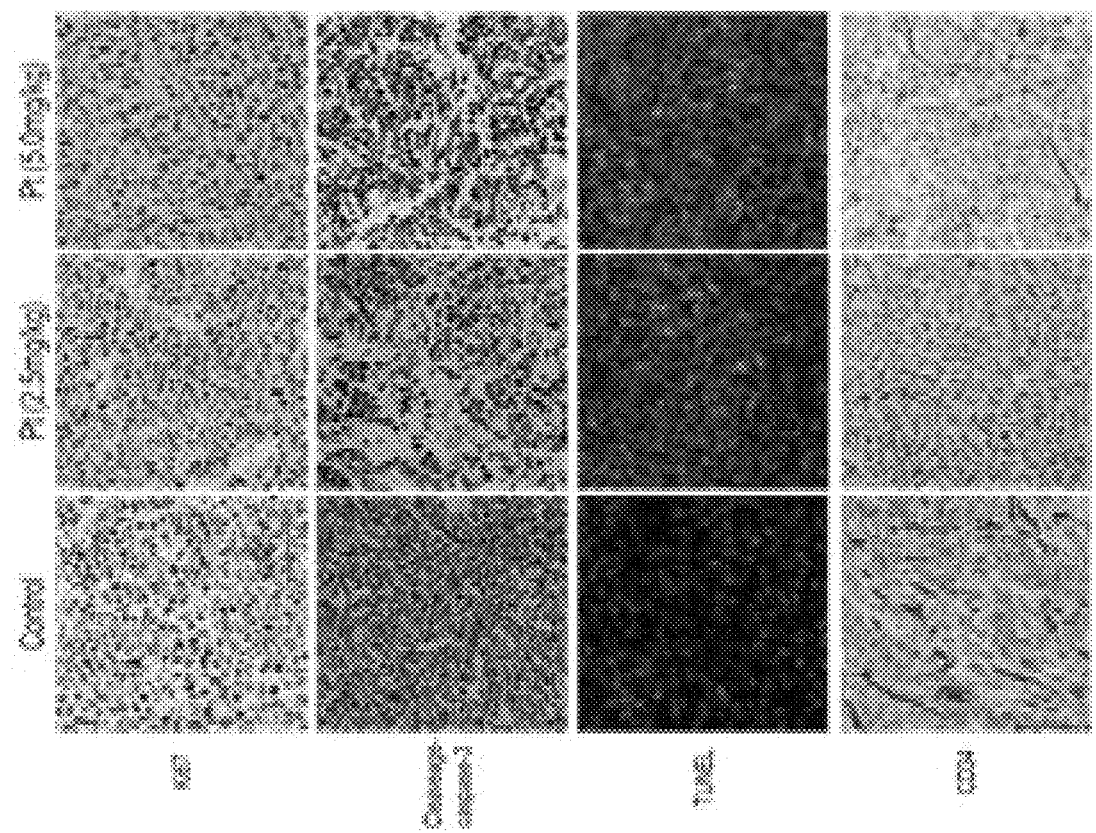

With the promising dual cytotoxic and anti-angiogenic properties of 1b, in vivo antitumor activity of 1b was investigated. Treatment of nude mice bearing MDA-MB-231 xenografts with 1b through intravenous injection once per two days resulted in a significant growth inhibition by 81 and 64% at concentration of 5 mg/kg and 2.5 mg/kg respectively, as compared to mice treated with solvent control (both with $p<0.01$; FIG. 15(A)). Importantly, 1b did not cause any death or body weight loss of mice during the treatment (FIG. 15(B)). Immunohistochemical analysis of tumor tissues from treated mice revealed decrease in expression of Ki67 as compared to those from control mice, suggesting the promising anti-proliferation effect of 1b (FIG. 15(C)). In addition, higher levels of caspase-3 and DNA fragmentation (as shown by TUNEL assay) were found in tumor tissues of treated mice, demonstrating the effective killing of cancer cells by 1b in vivo (FIG. 15(C)). More interestingly, CD34 staining, which can serve as marker for in vivo angiogenesis,[44] showed significant inhibition of blood vessel formation in tumors of treated mice (FIG. 15(C)). Taken together, 1b should be the first platinum(II) compound, according to the best of our knowledge, showing anti-proliferation, anticancer and anti-angiogenic effects in vivo.

As a promising candidate for treating cancer in vivo, we further investigate systemic toxicity from 1b. Blood biochemistry of nude mice after treatment with 1b (5 mg/kg, 2.5 mg/kg) showed low systemic toxicity of 1b (FIGS. 15(D)-(H)); plasma levels of several organ damage indicators including aspartate aminotransferase (AST), creatine kinase (CK) and blood fat (CHOL) of the treated mice were lower than those of the untreated mice bearing MDA-MB-231 xenografts ($p<0.05$; FIGS. 15(D), (E), (F)), fell within the statistically relevant range of those of mice without the xenografts. On the other hand, treated mice showed higher level of blood urea nitrogen (BUN) and blood glucose (GLU) level than untreated mice bearing MDA-MB-231 xenografts (FIGS. 15(G), (H)), suggesting that the treatment helped to recover the BUN and GLU level to almost healthy level.

Discussion

Disclosed herein are dual cytotoxic and anti-angiogenic compounds should be new candidates for treating aggressive and highly metastatic cancers which are almost non-curable in this moment. Although platinum(II) compounds are known for their good potency in killing cancer cells, it is quite surprising that anti-angiogenic platinum(II) compounds are less well known and none of the reported platinum(II) compounds demonstrate dual cytotoxic and anti-angiogenic activities in vivo. This can be due to the strong binding of square-planar platinum(II) compounds onto DNA, thus they show less tendency to interact with other biomolecules in tumor microenvironment and hence they are not anti-angiogenic. In order to target other biomolecules, NHC ligands were introduced onto the complexes in order to weaken the interactions of the complexes with DNA by the out-of-plane NHC ligands. Proteomics data and in vitro biochemical assays indicate significant effect of 1b on uPA/uPAR- and VEGF-mediated signaling pathway, further suggesting that 1b can likely interact with biomolecules in tumor microenvironment.

In addition, since NHC is a strong G-donor and can increase the energy level of non-emissive ligand-field (LF) state, the platinum(II) NHC complexes are strongly luminescent and displaying vibronic structured emission spectra upon photo excitation.[24] Due to their luminescence properties, cellular distribution of the complexes can be examined by confocal fluorescence spectroscopy. 1b is found to preferentially accumulate in ER domain of HeLa cells and this information helped us to unravel the mechanism of action of these anticancer complexes: induction of ER stress and subsequent apoptotic cell death. Also, it is conceivable that such strong luminescence can render the metal complexes being both diagnostic and therapeutic agents, i.e. theranostics, and hence real-time monitoring of treatment by the complexes can be feasible.

The promising in vitro and in vivo anticancer activities of this class of platinum(II) complexes are attributable to their dual cytotoxic and anti-angiogenic properties. Their high cytotoxicity against a panel of cancer cells, including highly metastatic MDA-MB-231, can be explained by induction of ER stress, as supported by up regulation of phosphorylated RNA-dependent protein kinase-like endoplasmic reticulum kinase (PERK), phosphorylated eukaryotic initiation factor 2a (eIF2α) and C/EBP homologous protein (CHOP) in western blotting analysis. In addition, DNA fragmentation and mitochondria dysfunction are found in the treated cells, as shown by G0/G1 cell-cycle arrest and increase of cell population in sub-G1 phase, and JC1 staining assay respectively. On the other hand, the anti-angiogenic properties of the complexes are first revealed by proteomic analysis on 1b-treated MDA-MB-231 cells, showing that CHIP, c-Kit and VHL protein pathway are the most predominantly modulated pathways and they are all closely related to angiogenic responses of cancer cells. The involvement of 1b in regulation of angiogenesis is further supported by western blotting and in vitro experiments including wound closure assay, transwell invasive and tube formation assay. More importantly, 1b demonstrates excellent ex vivo and in vivo anti-angiogenic properties in chorioallantoic membrane (CAM) assay and immunohistochemical analysis of tumor tissues from treated mice bearing MDA-MB-231 xenograft, respectively. Taken together, treatment of mice bearing highly metastatic MDA-MB-231 xenograft by 1b results in remarkable inhibition of tumor growth, and anti-proliferation and anticancer effects as found in immunohistochemical analysis. Interestingly, there is no significant loss in body weight or death of mice throughout the treatment and blood biochemistry indicates low systemic toxicity of 1b, further demonstrating the potential of this class of [Pt(BPI)(NHC)]$^+$ complexes for treating highly metastatic cancers. The promising dual cytotoxic and anti-angiogenic effects in vivo should be firstly found in platinum(II) compounds, according to the best of our knowledge, and the unique chemical structure of the complexes with out-of-plane NHC ligands for prohibiting strong interactions with DNA can probably accounted for the dual properties.

Dual cytotoxic and anti-angiogenic [Pt(BPI)(NHC)](OTf) were synthesized and characterized. They were cytotoxic against various cancer cells, and this was ascribed to apoptotic cell death induced by ER-stress, mitochondria dysfunction and cell cycle arrest. Proteomic data indicated regulation of angiogenesis by the platinum(II) complexes. Such unique feature allows these complexes to slow down extracellular matrix proteolysis process by inhibiting uPA and MMP expressions. Also, this could inhibit downstream signaling pathways of uPA/uPAR and protect native VEGF from cleavage, thereby accounting for the promising in vitro and ex vivo anti-angiogenic properties of the complexes (FIG. 16). Significant inhibition of in vivo tumor growth in nude mice bearing MDA-MB-231 xenografts by 1b was also demonstrated, with minimal systemic toxicity found as indicated by blood biochemistry. Immunohistochemical analysis of tumor tissues from treated mice revealed promising anti-proliferation, anticancer and anti-angiogenic effects of 1b in vivo.

6.2 Materials and Methods

All of the starting materials for synthesis came from commercially available resources such as Sigma Aldrich, Alfa Aesar and Apollo Scientific companies. The solvents used were at least in analytical grade. Elemental analysis was done by Dr. Zong of the Institute of Chemistry at the Chinese Academy of Science located in Beijing. 1H NMR spectra were recorded on Bruker FT-400M Hz or 300M Hz NMR spectrometers with tetramethylsilane as the reference. Fast atom bombardment (FAB) mass spectra were obtained on a Finnigan Mat 95 mass spectrometer. Perkin-Elmer Lambda 19 UV-vis spectrophotometer was used for UV-vis spectral analysis.

Fluorescence images were taken using Carl Zeiss LSM 510 Meta/Axiocam confocal microscopy. For MTT and protein assays, the absorbance was quantified by using a Perkin Elmer Fusion Reader (Packard BioScience Company).

The BPI (1,3-Bis(2-pyridylimino)isoindoline), benz(f)BPI (3-Bis(2-pyridylimino)benz(f)isoindoline) and Pt(BPI)Cl were synthesized according to reported procedures.[47]

6.3 Compound Characterization

Synthesis of 1,3-Bis(2-pyridylimino)isoindoline (BPI):[47]

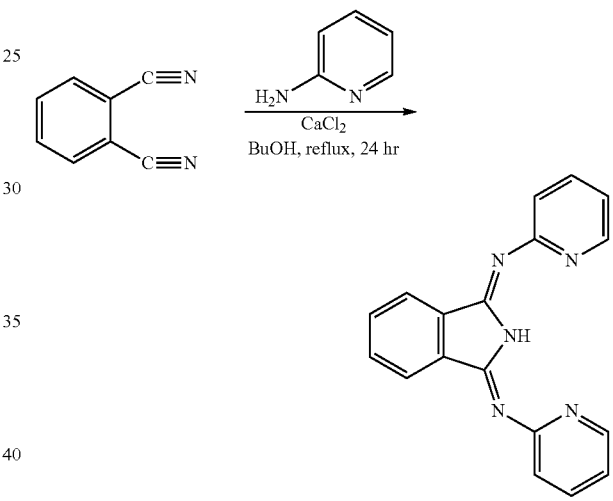

A mixture of phthalonitrile (1 g, 7.81 mmol), 2-aminopyridine (1.47 g, 15.62 mmol), and CaCl$_2$ (78.6 mg, 0.7 mmol) in 1-butanol (50 mL) was refluxed for 1 day. After cooling to room temperature, the resulting pale yellow precipitate was filtered off. Then, the crude product was purified by chromatography on a silica gel column using dichloromethane/methanol (200:1, v/v) as the eluent. Yield: 54%.

Synthesis of
3-Bis(2-pyridylimino)benz(f)isoindoline
(benz(f)BPI)

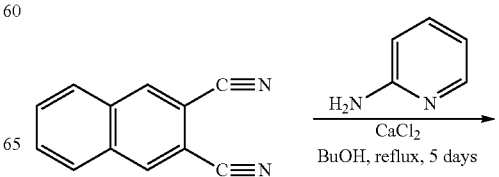

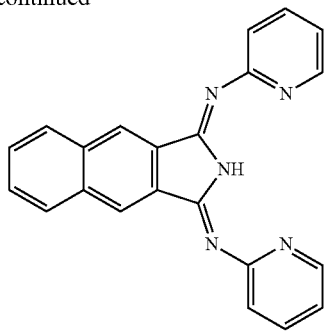

A mixture of naphthalene-2,3-dicarbonitrile (1.39 g, 7.81 mmol), 2-aminopyridine (1.47 g, 15.62 mmol), and CaCl$_2$ (78.6 mg, 0.7 mmol) in 1-butanol (50 mL) was refluxed for 5 days. After cooling to room temperature, the resulting pale yellow precipitate was extracted to dichloromethane layer. Then, the crude product was purified by chromatography on a silica gel column using hexane: ethyl acetate (5:1, v/v) as the eluent. Yield: 43%. $^1$H NMR (400 MHz, CDCl$_3$): δ=8.65-8.64 (m, 2H), 8.60 (s, 2H), 8.09-8.06 (m, 2H), 7.81-7.77 (m, 2H), 7.64-7.61 (m, 2H), 7.51-7.49 (m, 2H), 7.16-7.13 (m, 2H).

Synthesis of Pt(BPI)Cl (1i)

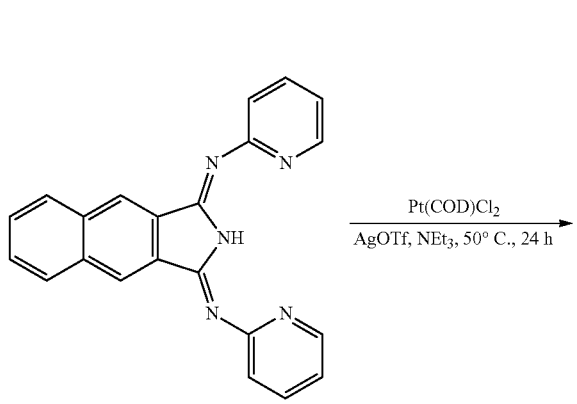

Silver triflate (0.138 g, 0.54 mmol) was added dropwise into Pt(COD)Cl$_2$ (0.1 g, 0.26 mmol) in methanol (15 mL). After stirring for 15 min, the mixture was filtered off and added into BPI (88 mg, 0.29 mmol) in methanol (15 mL). Then, triethylamine (27 mg, 0.26 mmol) was added into reaction mixture and it was heated to 50° C. for 24 h. After cooling to room temperature, the crude product was extracted into dichloromethane layer. Finally, the red solid was washed with ether. Yield: 42%. $^1$H NMR (400 MHz, CDCl$_3$): δ=10.32-10.29 (m, 2H), 8.59 (s, 2H), 8.09-8.03 (m, 2H), 7.98-7.92 (m, 2H), 7.73-7.65 (m, 4H), 7.07-7.03 (m, 2H).

added into extend-BPI (101 mg, 0.29 mmol) in methanol (15 mL). Then, triethylamine (27 mg, 0.26 mmol) was added into reaction mixture and it was heated to 50° C. for 24 h. After cooling to room temperature, the crude product was extracted into dichloromethane layer. Finally, the yellow solid was washed with ether. Yield: 64%. $^1$H NMR (400 MHz, CDCl$_3$): δ=10.37-10.35 (m, 2H), 8.13-8.10 (m, 2H), 7.94-7.90 (m, 2H), 7.63-7.67 (m, 4H), 7.01-7.04 (m, 2H).

Synthesis of Pt (N^N^N)Cl

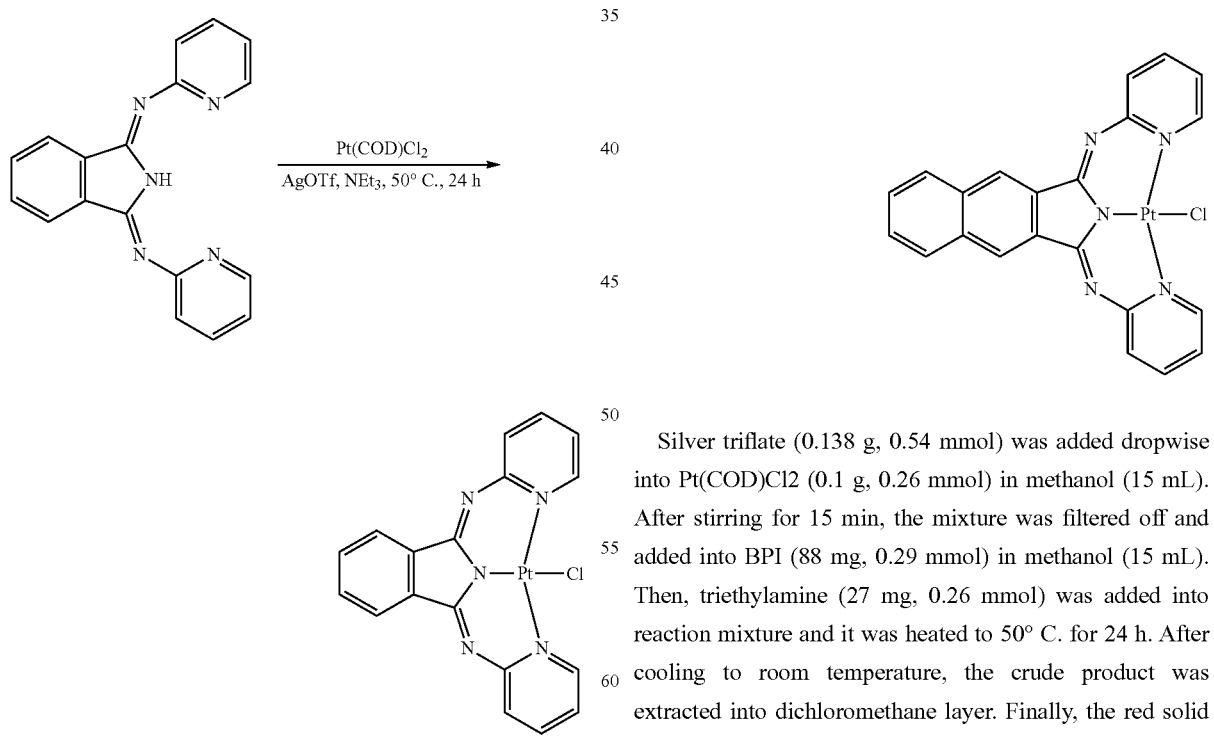

Silver triflate (0.138 g, 0.54 mmol) was added dropwise into Pt(COD)Cl2 (0.1 g, 0.26 mmol) in methanol (15 mL). After stirring for 15 min, the mixture was filtered off and

Synthesis of 1a

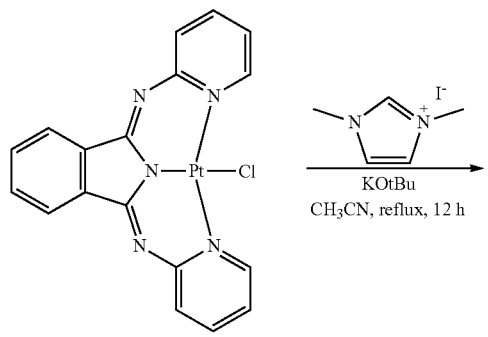

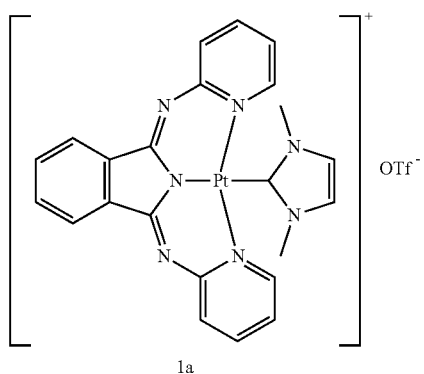

A mixture of [Pt(BPI)Cl] (50 mg, 0.095 mmol), potassium tert-butoxide (10.6 mg, 0.095 mmol) and 1,3-dimethyl-1H-imidazol-3-ium iodide (23.4 mg, 0.104 mmol) in acetonitrile (15 mL) was heated to reflux for 12 hours. After cooling to room temperature, silver trifluoromethanesulfonate (84 mg, 0.33 mmol) was added into reaction mixture and stirred for 30 min. After extracting the crude product into dichloromethane layer, it was purified by column chromatography on silica gel with $CH_3CN/CH_2Cl_2$ (3:1, v/v) as eluent, and yellow powder was obtained.

Yield 52%; $^1$H NMR (400 MHz, $CD_3CN$): δ=8.17-8.15 (m, 2H), 8.02 (t, 2H, J=8.0 Hz), 7.80-7.82 (d, 2H, J=4.0 Hz), 7.70-7.72 (m, 2H), 7.60 (s, 2H), 7.42-7.40 (d, 2H, J=4.0 Hz), 7.02 (t, 2H, J=8.0 Hz), 3.98 (s, 6H); MS (FAB, +ve): m/z 589 [M-OTf]$^+$; Elemental analysis calcd (%) for $C_{24}H_{20}F_3N_7O_3PtS$: C, 39.03; H, 2.73; N, 13.27. found: C, 38.75; H, 2.80; N, 13.22.

Synthesis of 1b

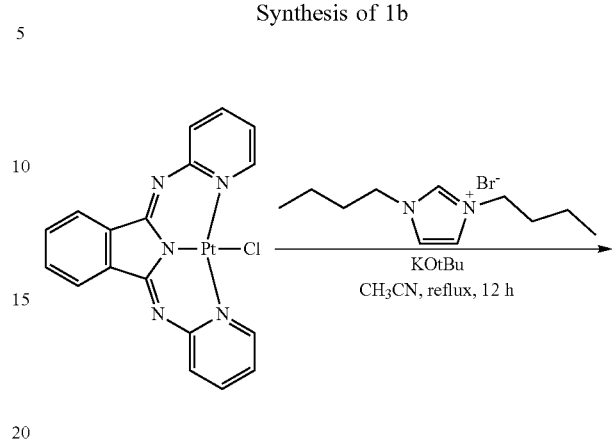

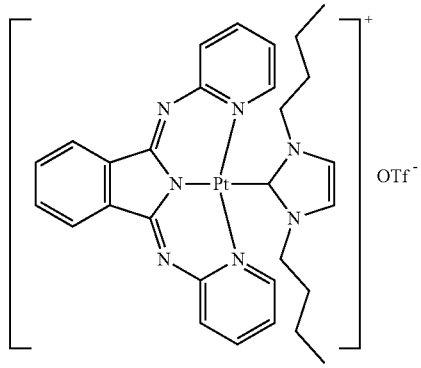

The procedure is similar to that for 1a.

Yield 61%; $^1$H NMR (400 MHz, $CDCl_3$): δ=8.17-8.16 (m, 2H), 8.06-8.02 (m, 2H), 7.84-7.82 (m, 2H), 7.74-7.72 (m, 2H), 7.62-7.61 (m, 2H), 7.44-7.42 (m, 2H), 7.04-7.00 (m, 2H), 4.38 (t, 4H, J=8.0 Hz), 1.76-1.68 (m, 4H), 1.31-1.22 (m, 4H), 0.77-0.72 (m, 6H); MS (FAB, +ve): m/z 673 [M-OTf]$^+$; Elemental analysis calcd (%) for $C_{30}H_{32}F_3N_7O_3PtS$: C, 43.79; H, 3.92; N, 11.92. found: C, 43.64; H, 4.05; N, 11.82.

Synthesis of 1c

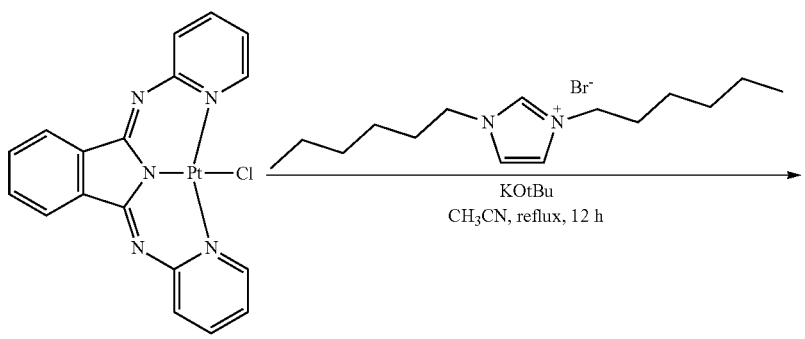

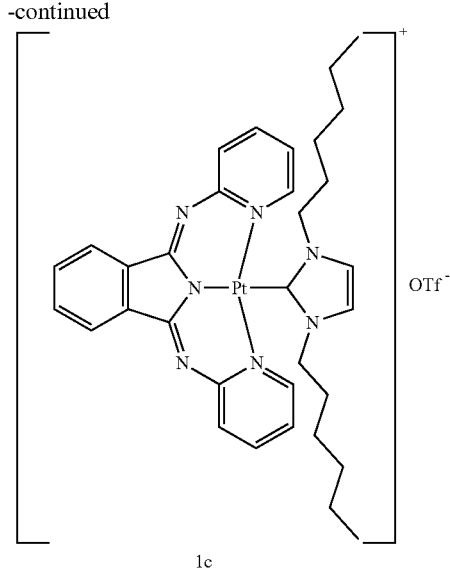

1c

The procedure is similar to that for 1a.

Yield 49%; $^1$H NMR (400 MHz, CDCl$_3$): δ=8.20-8.14 (m, 2H), 8.08-8.02 (m, 2H), 7.88-7.82 (m, 2H), 7.78-7.72 (m, 2H), 7.62-7.60 (m, 2H), 7.42-7.38 (m, 2H), 7.02-6.96 (m, 2H), 4.35 (t, 4H, J=8.0 Hz), 1.78-1.66 (m, 4H), 1.28-1.16 (m, 4H), 1.14-1.04 (m, 8H), 0.78-0.70 (m, 6H); MS (FAB, +ve): m/z 729 [M-OTf]$^+$; Elemental analysis calcd (%) for C$_{35}$H$_{43}$F$_3$N$_7$O$_3$PtS.0.5H$_2$O: C, 46.56; H, 4.91; N, 10.86. found: C, 46.38; H, 4.71; N, 11.00.

3H), 7.46-7.43 (m, 3H), 7.04-7.01 (m, 2H), 4.28 (t, 2H, J=4.0 Hz), 4.06 (s, 3H), 1.16-1.07 (m, 12H), 0.77 (t, 3H, J=8.0 Hz); MS (FAB, +ve): m/z 687 [M-OTf]$^+$; Elemental analysis calcd (%) for C$_{30}$H$_{36}$F$_3$N$_7$O$_3$PtS: C, 43.58; H, 4.39; N, 11.86. found: C, 43.79; H, 4.15; N, 11.53.

Synthesis of 1d

Synthesis of 1e

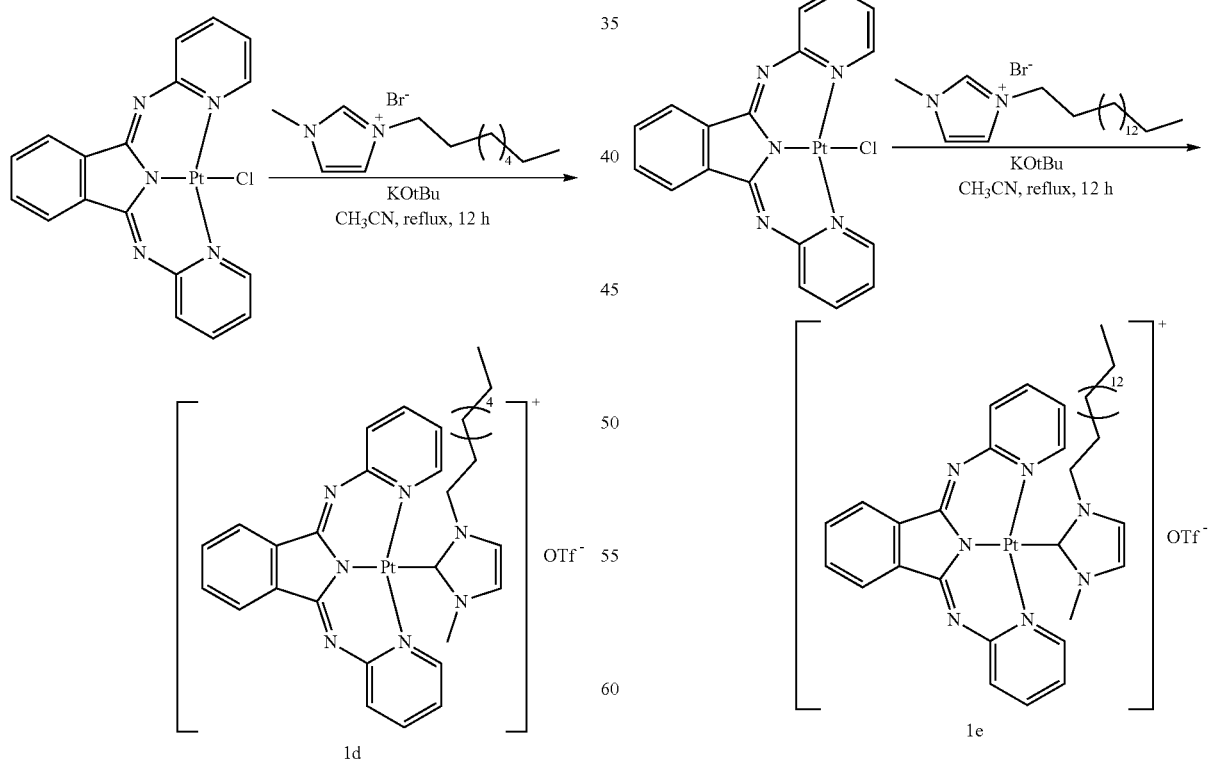

1d

1e

The procedure is similar to that for 1a.

Yield 51%; $^1$H NMR (500 MHz, CDCl$_3$): δ=8.17-8.15 (m, 2H), 8.04-8.00 (m, 2H), 7.86-7.80 (m, 2H), 7.74-7.72 (m, The procedure is similar to that for 1a.

Yield 44%; $^1$H NMR (300 MHz, CDCl$_3$): δ=8.20-8.14 (m, 2H), 8.06-7.96 (m, 2H), 7.86-7.78 (m, 2H), 7.76-7.70 (m, 3H), 7.48-7.42 (m, 3H), 7.06-7.00 (m, 2H), 4.28 (t, 2H, J=6.0 Hz), 4.06 (s, 3H), 1.35-1.04 (m, 28H), 0.88 (t, 3H, J=6.0 Hz). MS (FAB, +ve): m/z 799 [M-OTf]$^+$; Elemental analysis calcd (%) for $C_{38}H_{52}F_3N_7O_3PtS$: C, 48.61; H, 5.58; N, 10.44. found: C, 49.01; H, 5.50; N, 10.23.

Synthesis of 1f

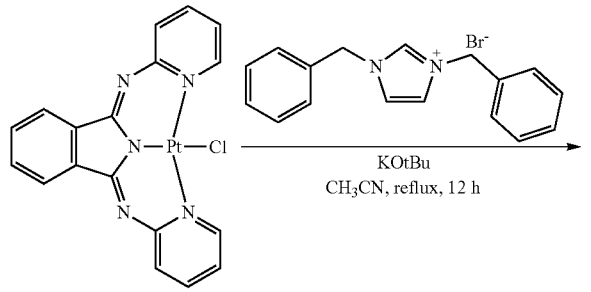

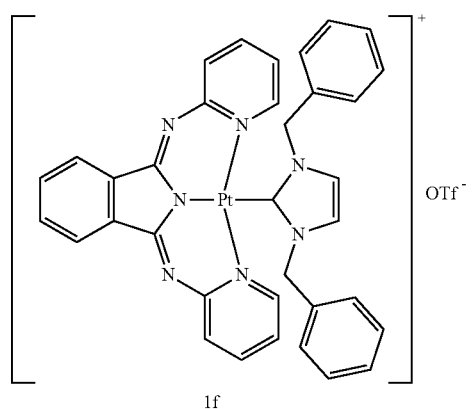

The procedure is similar to that for 1a.

Yield 45%; $^1$H NMR (400 MHz, CD$_3$CN): δ=8.16-8.14 (m, 2H), 7.93-7.91 (m, 2H), 7.81-7.79 (m, 2H), 7.68-7.66 (m, 4H), 7.26-7.24 (m, 4H), 7.06-6.98 (m, 8H), 6.60-6.54 (m, 2H), 5.42 (s, 4H); MS (FAB, +ve): m/z 741[M-OTf]$^+$; Elemental analysis calcd (%) for $C_{36}H_{28}F_3N_7O_3PtS\cdot CHCl_3$: C, 43.99; H, 2.89; N, 9.71. found: C, 44.07; H, 2.97; N, 9.89.

Synthesis of 1g

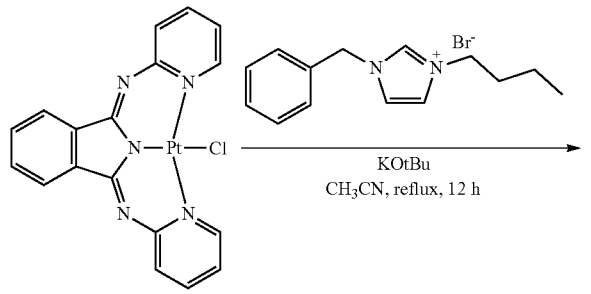

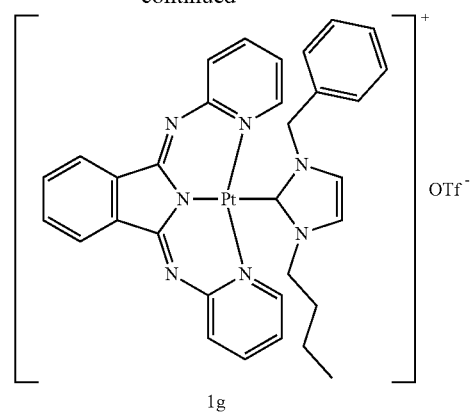

The procedure is similar to that for 1a.

Yield 49%; $^1$H NMR (400 MHz, CDCl$_3$): δ=8.17-8.12 (m, 2H), 8.08-8.02 (m, 2H), 7.80-7.78 (m, 2H), 7.74-7.73 (m, 2H), 7.65-7.62 (m, 1H), 7.54-7.53 (m, 1H), 7.27-7.25 (m, 2H), 7.17-7.15 (m, 2H), 7.04-6.99 (m, 3H), 6.77-6.74 (m, 2H), 5.44-5.42 (m, 2H), 4.33-4.29 (m, 2H), 1.74-1.62 (m, 2H), 1.24-1.15 (m, 2H), 0.72-0.68 (m, 3H); MS (FAB, +ve): m/z 707 [M-OTf]$^+$; Elemental analysis calcd (%) for $C_{33}H_{30}F_3N_7O_3PtS$: C, 46.26; H, 3.53; N, 11.44. found: C, 46.17; H, 3.55; N, 11.14.

Synthesis of 1h

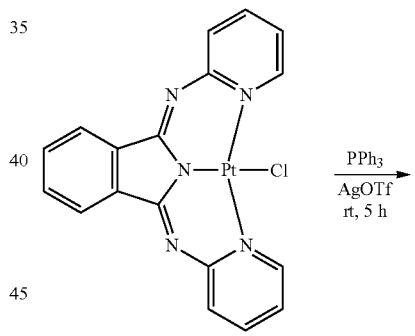

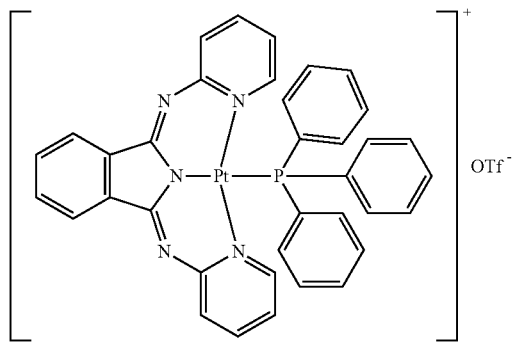

Silver trifluoromethanesulfonate (24.4 mg, 0.095 mmol) was added into a mixture of [Pt(BPI)Cl] (50 mg, 0.095 mmol) and triphenylphosphine (30 mg, 0.114 mmol) in dichloromethane:acetonitrile (20 mL; 1:1, v/v). The reaction mixture was stirred at room temperature for 5 hours.

After extracting the crude product into dichloromethane layer, it was purified by recrystallization by diffusing diethyl ether into acetonitrile. Reddish yellow crystal was obtained.

Yield 39%; $^1$H NMR (400 MHz, CDCl$_3$): δ=8.71-8.69 (m, 2H), 8.16-8.15 (m, 2H), 7.86-7.78 (m, 9H), 7.58-7.52 (m, 6H), 7.48-7.46 (m, 6H), 6.62-6.58 (m, 2H). $^{31}$P NMR (400 MHz, CDCl$_3$): δ=12.27. Elemental analysis calcd (%) for C$_{37}$H$_{27}$F$_3$N$_5$O$_3$PPtS: C, 49.12; H, 3.01; N, 7.74. found: C, 48.98; H, 3.02; N, 7.99.

Synthesis of 1j

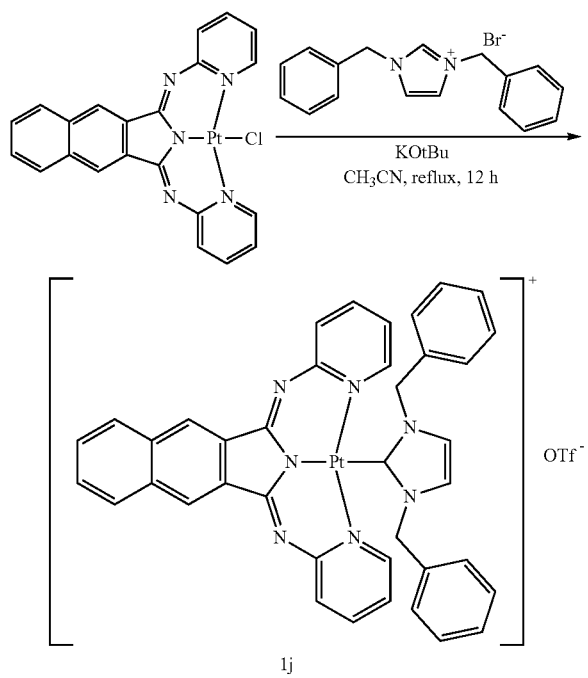

The procedure is similar to that for 1a.

Yield 47%; $^1$H NMR (400 MHz, CDCl$_3$): δ=8.68 (s, 2H), 8.16-8.14 (m, 2H), 7.88-7.86 (m, 2H), 7.74-7.72 (m, 6H), 7.24-7.22 (m, 4H), 7.12-7.04 (m, 8H), 6.67-6.64 (m, 2H), 5.53 (s, 4H); MS (FAB, +ve): m/z 791 [M-OTf]$^+$; Elemental analysis calcd (%) for C$_{40}$H$_{31}$F$_3$N$_7$O$_3$PtS: C, 51.01; H, 3.32; N, 10.41. found: C, 50.85; H, 3.02; N, 10.15.

6.4 Experimental Procedure

6.4.1 Cell Culture

The cell lines were maintained in cell culture media (Minimum essential medium (MEM) for HeLa; and Dulbecco's modified eagle medium (DMEM) for MDA-MB-231 and MiHa, Roswell Park Memorial Institute (RPMI) medium for NCI-H460 and HCT116 supplemented with fetal bovine serum (10 vol %), streptomycin (100 µg/ml) and penicillin (100 U/ml) in an incubator (5% CO$_2$) at 37° C.

Human umbilical vein endothelial cells (HUVEC) were cultured in endothelial cell growth medium (ECGM): M199 medium (Life Technologies, Invitrogen) supplemented with 15 vol % fetal bovine serum at 37° C. in a humidified (5% CO$_2$, 95% air) atmosphere.

6.4.2 MTT Assay

The inhibition of cell growth by different metal complexes were determined by MTT assay. Firstly, 4×10$^3$ to 8×10$^3$ cells were seeded on 96-well culture plates for 24 h. Then, different concentrations of complex was added into different wells by serial dilution and the cells were incubated with complex for 48-72 h. After that, 10 µl of MTT solution (5 mg/ml) was added per well and the plate was incubated for 4 h at 37° C. in a humidified atmosphere of 5% CO$_2$. Viable cells with active metabolism converted MTT into a purple colored formazan product. In order to solubilize the formazan for absorbance readings, 100 µl of SDS (0.1 g/ml, 0.01 M HCl) was added per well and the plate was kept in a dark and humidified chamber overnight. Finally, the absorbance at 580 nm of each well was monitored by microtiter plate reader.

The growth inhibition by a specific complex was represented by IC$_{50}$ (concentration of a complex causing 50% inhibition of cell growth). Each experiment was repeated three times and the results were expressed as means±standard deviation (SD).

6.4.3 Scratch Assay (Wound-Healing Assay)

MDA-MB-231 cells were cultured in 6-well plate and allowed to form a confluent monolayer for 24 h. After serum starved for 4 h, cells were scratched by pipette tips, washed with PBS and photographed by using a fluorescence microscope (20× objective). The fresh medium supplemented with 10 vol % FBS was added into each well with different concentrations of Pt complex. After incubated for 24 h, cells were photographed again at three random areas. Then the migrated cells were quantified by manual counting and inhibition ratio was expressed as % of control.

6.4.4 Transwell Invasion Assay

Effects of Pt complex on the invasion of MDA-MB-231 or HUVECs cells were performed on Transwell Boyden chamber (8 µm pore, Corning, Lowel, Mass.) pre-coated with matrigel for 4 h at 37° C. The cell suspension (2.5×10$^5$ cells/ml, 100 µL) in serum free medium (SFM) was placed to the upper compartment of chamber. The bottom chambers were supplemented with 500 µl complete medium (10 vol % FBS) or conditioned medium (with VEGF=13.4 ng/ml from MDA-MB-231 cells) containing indicated concentrations of Pt complex. After incubated for 24 h, the non-migrant cells from the upper face were scraped using a cotton swab. The invaded cells on the lower face were fixed with methanol, stained with Giemsa, photographed by a phase-contrast microscope (200×, Nikon TS 100). The invaded cells were quantified by manual counting and inhibition ratio was expressed as % of control.

6.4.5 Tube Formation Assay

The In Vitro Angiogenesis Kit (CaymanChemical) was used in the tube formation assay. Firstly, the ECMatrix solution and 10× Diluent Buffer were mixed in 9:1 (v/v) ratio on ice. Then 50 µL of mixture was transferred into each well of 96-well plate and incubated at 37° C. for 1 h for polymerization. Then, around 4×10$^4$ of MS-1 cells in 100 µL DMEM medium was pre-mixed with different concentrations of complex and that cell-complex containing medium was added on the top of the polymerized matrix. After 2 h, the tube formation was observed under an inverted microscopy at a 50× magnification.

At the same time, the cell viability under the same condition was determined by MTT assay. Again, around $4\times10^4$ MS-1 cells in 100 μL DMEM medium was pre-mixed with different concentrations of complex and they were seeded into 96-well plate. After 2 h, the medium was removed and fresh medium with 10% MTT was added per well and the plate was incubated for 4 h at 37° C. in a humidified atmosphere of 5% CO2. In order to solubilize the formazan for absorbance readings, 100 μl of SDS (0.1 g/ml, 0.01 M HCl) was added per well and the plate was kept in a dark and humidified chamber overnight. Finally, the absorbance at 580 nm of each well was monitored by microtiter plate reader. Each experiment was repeated three times and the results were expressed as means±standard deviation (SD).

6.4.6 Confocal Fluorescence Microscopy

HeLa cells ($2\times10^5$ cells) were seeded in a one chamber slide (Nalgene; Nunc) with culture medium (2 mL per well) and incubated at 37° C. in a humidified atmosphere of 5% $CO_2$/95% air for 24 h. After treating with 1b (5 μM) for 1 h, ER-tracker™ red (1 μM), Mitotracker® deep red (50 nM) or Lysotracker® deep red (50 nM) were incubated with cells for 10 min, and then the cells were washed with PBS twice. Confocal fluorescence images were captured using a Carl Zeiss LSM510 Meta confocal microscope with the use of 488 and 543 nm/633 nm lasers for the excitation of complex 1b and red/deep red tracker respectively, under a Plan-Apochromat 63×1.40NA oil-immersion objective.

6.4.7 Determination of Extracellular VEGF

The concentrations of extracellular VEGF was determined by Quantikine® ELISA kit (R&D System). Briefly, cells were cultured in 6-well plate for 24 h, washed with PBS twice and replaced with fresh serum-free medium containing different concentrations of Pt complex. After 24 h treatment, the culture media were collected and centrifuged to eliminate cellular debris. Then, the collected medium was added into the detected microplate and incubates for 2 h at room temperature. After three washes, the VEGF conjugate was added and incubated for another 2 h. After another three washes and the addition of substrate solution and stop solution, the detection of VEGF concentration in the culture medium was performed by monitoring absorption at 450 nm using a microplate spectrophotometer (VERSA max, Molecular Devices).

6.4.8 Chorioallantoic Membrane Assay

The effect of Pt complex on the ex vivo angiogenesis was determined by chorioallantoic membrane (CAM) assay. Briefly, fertilized chicken eggs were incubated at 37° C. in a humidified incubator with forced air circulation. After 5-6 days, eggs were cracked open and methylcellulose discs containing different concentrations of 1d (40 μl/egg) and VEGF (50 ng/mL) were gently implanted on top of chicken CAM. After one day incubation, the CAM was observed under a microscope (Olympus BX 40) and photographed. VEGF treatment group was used as a positive control. Three eggs per group were used in each experiment and three independent experiments were performed.

6.4.9 Flow Cytometric Analysis

The effects of 1d on the cell cycle progression and the induction of apoptotic cell death were quantified by flow cytometric analysis. Briefly, treated or untreated cells were trypsinized, washed with PBS and fixed with 70% ethanol overnight at −20° C. The fixed cells were washed with PBS and incubated with a PI working solution for 4 h in darkness. The stained cells were analyzed by flow cytometer (Beckman Coulter, Fullerton, Calif.). Cell cycle distribution was analyzed using MultiCycle software (Phoenix Flow Systems, San Diego, Calif.). The proportion of cells in G0/G1, S, and G2/M phases was represented as DNA histograms. Apoptotic cells with hypodiploid DNA content were measured by quantifying the sub-G1 peak in the cell cycle pattern. For each experiment, over 10,000 events per sample were recorded.

6.4.10 Western Blotting

MDA-MB-231 cells ($5\times10^5$ cells) were incubated with Pt compound and washed with phosphate-buffered saline (PBS), lysed with radioimmunoprecipitation assay buffer (1% Triton X-100, 10% glycerol, 150 mM NaCl, 5 mM sodium fluoride, 1 mM sodium vanadate and protein inhibitor cocktail) for 15 min at 4° C. The cell lysates were centrifuged at 13,000 rpm for 15 min at 4° C. The protein concentrations of the extracts were determined using a BCA protein assay kit (Beyotime, Haimen, China). Specific amount of protein sample (30 μg) was then boiled for 5 min in a 5× sample buffer (50 mM Tris (pH 7.4), 4% sodium dodecyl sulfate (SDS), 10% glycerol and 50 μg/mL bromophenol blue) at a volume ratio of 4:1. Protein samples were subjected to SDS-polyacrylamide gel electrophoresis (PAGE), transferred to polyvinylidene difluoride membranes and immunoblotted with primary anti-bodies. After further incubation with horseradish peroxidase (HRP)-conjugated secondary antibody, the blot was stained with a chemiluminescent detection reagent and subsequently analyzed by enhanced chemiluminescence. Protein expression was visualized on Kodak Biomax X-ray film.

6.4.11 Statistic Analysis

Experiments were conducted at least three times and data was expressed as mean±standard deviation (SD). Statistical analysis was performed on SPSS statistical program version 13 (SPSS Inc., Chicago, Ill.). Difference between two groups was analyzed by two-tailed Student's t test and that between three or more groups was analyzed by one-way ANOVA multiple comparisons. Difference with $P<0.05$ (*) or $P<0.01$ (**) was considered to be statistically significant.

6.4.12 Proteomic Studies

Sample preparation. MDA-MB-231 cells ($8\times10^5$ cells) were incubated with 5 μM of 1d or DMSO for 5 h under 5% $CO_2$ environment at 37° C. The cells were then washed with PBS to remove excess compound and lysed with urea lysis buffer (20 mM Tris-HCl, 8 M urea, protein phosphatase inhibitor cocktail, pH 8.0). The cell lysates were centrifuged at 13,000 rpm for 15 min at 4° C. Specific amount of protein sample (50 μg) were then precipitated by adding 4× volume of ice-cold acetone and stored at −20° C. for 4 h. The precipitated proteins were centrifuged at 13,000 rpm for 20 min at 4° C. and the acetone solvent were discarded. After that, the protein pellets were dried by SpeedVac (Thermo Fisher Scientific) and re-suspended in 50 µL of urea buffer (100 mM Tris, 8 M urea, pH 8.5). Then, freshly prepared DTT (final concentration: 5 mM) was added into the sample to reduce to disulfide bond for 30 mins. Then, iodoacetamide (final concentration: 25 mM) was added to alkylate the reduced di-sulfide bond and the samples were kept in the dark for 30 min at 25° C. In order to dilute the urea concentration down to 2 M, around 140 µL of 100 mM Tris (pH 8.5) buffer was added into the sample. Then, 1 µg of trypsin was added into the sample mixture and it was kept at 37° C. overnight. About 10 µL of formic acid was added into sample mixtures to stop the digestion. After centrifugation at 14,000 rpm for 15 min, the supernatants were transferred to new eppendorf (can be frozen at −80° C. for long term storage). The resulting peptides were desalted and enriched by StageTips. For each sample, three biological replicates were prepared. The samples were re-dissolved with $H_2O$ (containing 0.1% formic acid, v/v) for subsequent MS analysis.

Hplc-Ms/Ms Analysis.

MS analysis was performed with a LTQ Orbitrap Velos Orbitrap mass spectrometer (Thermo Scientific) connected online with a HPLC. The analytical column was a self-packed PicoTip® column (360 µm outer diameter, 75 µm inner diameter, 15 µm tip, New Objective) packed with 10 cm length of C18 material (ODS-A C18 5-µm beads, YMC) with a high-pressure injection pump (Next Advance). The mobile phases of HPLC are A (0.1% formic acid in HPLC grade $H_2O$, volume percentage) and B (0.1% formic acid in HPLC grade acetonitrile, volume percentage). 3 µg of sample was loaded onto the analytical column by the autosampler and rinsed with 2% B for 6 min and subsequently eluted with a linear gradient B from 2% to 40% for 120 min. For the MS analysis, LTQ-Orbitrap Velos MS was operated in a data-dependent mode cycling through a high-resolution (6000 at 400 m/z) full scan MS1 (300-2000 m/z) in Orbitrap followed by CID MS2 scans in LTQ on the 20 most abundant ions from the immediate preceding full scan. The selected ions were isolated with a 2-Da mass window and put into an exclusion list for 60 seconds after they were first selected for CID.

Proteins Identification and Quantification.

The raw data were directly used for protein identification and quantification using MaxQuant (Version 1.5.3.30). The data were searched against uniprot human database (27 May 2016, 70625), in which trypsin specificity was used with up to two missed cleavages 17 allowed. Methionine oxidation was set as a variable modification, and iodoacetamide derivative of cysteine was set as a fixed modification. Default settings were used for mass tolerance for MS1 and MS2. The false discovery rate (FDR) was determined by searching against a reverse database and kept FDR at 1%. Peptides were quantified in a label-free manner using the area under the extracted ion chromatograph of peptides, and the protein abundances were the sum of the peptide abundances.

Signaling Pathway Analysis.

Lists of quantified proteins (shown as their Protein IDs) were uploaded to the ExPlain™ tool (version 3.1, BIOBASE) for further signaling pathway analysis. Details of procedure for pathway analysis have been described previously.[48,49]

6.4.13 In Vivo Tumor Growth Inhibition Experiments

All experiments were followed to the guidelines of the Laboratory Animal Unit of the University of Hong Kong. Ten mice were randomly divided into two groups (5 mice for each group) for two different treatment conditions.

Around $4 \times 10^6$ of cancer cells in 100 µL of PBS were injected into right back flanks of the mice through subcutaneous injection. After tumor formation (around 4 days), the treatment group was injected with drug at the dosage of 10 mg/kg and the control group was injected with solvent only. The size of the tumors were measured by a ruler every 2-3 days until the mice were sacrificed. The longest diameter (a) and shortest diameter (b) of the tumor would be picked up and the volume of the tumor could be calculated through the following formula:

$$V = 0.52 \times ab^2$$

It should be noted that the body weight of the mice were also be recorded in order to examine the side effect of the drugs.

To calculate the inhibition effect of the drug, the ratio of enlargement of tumor volume between the drug treatment group and control group would be applied in the following formula:

$$\text{Inhibition} = \left(1 - \frac{V_t - V_0}{V_t' - V_0'}\right) \times 100\%$$

where $V_t$ and $V_t'$ are the tumor volumes of drug treatment and control group respectively; $V_0$ and $V_0'$ are the tumor volume at the 0 day of drug treatment and control group respectively.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

REFERENCE

[1] Johnstone, T. C., Suntharalingam, K., Lippard, S. J. The Next Generation of Platinum Drugs: Targeted Pt(II) Agents, Nanoparticle Delivery, and Pt(IV) Prodrugs. *Chem. Rev.* 116, 3436-3486 (2016).

[2] Wheate, N. J., Walker, S., Craig, G. E., Oun, R. The status of platinum anticancer drugs in the clinic and in clinical trials. *Dalton Trans.* 39, 8113-8127 (2010).

[3] Jamieson, E. R., Lippard, S. J. Structure, recognition, and processing of cisplatin-DNA adduct. *Chem. Rev.* 99, 2467-2498 (1999).

[4] Jung, Y., Lippard, S. J. Direct cellular responses to platinum-induced DNA damage. *Chem. Rev.* 107, 1387-1407 (2007).

[5] Housman, G., Byler, S., Heerboth, S., Lapinska, K., Longacre, M., Snyder, N., Sarkar, S. Drug Resistance in Cancer: An Overview. *Cancers* (Basel). 6, 1769-1792 (2014).

[6] Kai Kessenbrock, Vicki Plaks, Zena Werb. Matrix Metalloproteinases: Regulators of the Tumor Microenvironment. *Cell.* 141, 52-67 (2010).

[7] Whiteside, T. L. The tumor microenvironment and its role in promoting tumor growth. *Oncogene.* 27, 5904-5912 (2008).

[8] Hicklin, D. J., Ellis, L. M. Role of the vascular endothelial growth factor pathway in tumor growth and angiogenesis. *J. Clin. Oncol.* 23, 1011-1027 (2005).

[9] Ferrara, N., Gerber, H. P., LeCouter, J. The biology of VEGF and its receptors. *Nat. Med.* 9, 669-676 (2003).

[10] Noh, H., Hong, S. G., Huang, S. Role of Urokinase Receptor in Tumor Progression and Development. *Theranostics.* 3, 487-495 (2013).

[11] Mehlen, P., Puisieux, A. Metastasis: a question of life or death. *Nat. Rev. Cancer.* 6, 449-458 (2006).

[12] Lisa M. Coussens, Barbara Fingleton, Lynn M. Matrisian. Matrix Metalloproteinase Inhibitors and Cancer—Trials and Tribulations. *Science.* 295, 2387-2392 (2002).

[13] Paraic A. Kenny, Genee Y. Lee, Mina J. Bissell. Targeting the tumor microenvironment. *Front Biosci.* 12, 3468-3474 (2007).

[14] Vacca, A, Bruno, M., Boccarelli, A. Coluccia, M., Ribatti, D., Bergamo, A., Garbisa, S., Sartor, L., Sava, G. Inhibition of endothelial cell functions and of angiogenesis by the metastasis inhibitor NAMI-A. *British J. of Cancer.* 86, 993-998 (2002).

[15] (a) Nazarov, A. A., Nowak-Sliwinska, P., van den Bergh, H., Dyson, P. J., Nazarov, A. A., Nowak-Sliwinska, P., van Beijnum, J. R., Griffioen, A. W. Ruthenium clusters as new class of anti-angiogenic agent. *J. Biol. Inorg. Chem.* 19, S647-S647 (2014). (b) Nowak-Sliwinska, P., van Beijnum, J. R., Casini, A., Nazarov, A. A., Wagnieres, G., van den Bergh, H., Dyson, P. J., Griffioen, A. W. Organometallic ruthenium(II) arene compounds with antiangiogenic activity. *J. Med. Chem.* 54, 3895-3902 (2011). (c) Liu, L.-J., Lin, S., Chan, D. S.-H., Vong, C. T., Hoi, P. M., Wong, C.-Y., Ma, D.-L., Leung, C.-H. A rhodium(III) complex inhibits LPS-induced nitric oxide production and angiogenic activity in cellulo. *J. Inorg. Biochem.* 140, 23-28 (2014).

[16] (a) Ott, I., Qian, X. H., Xu, Y. F., Vlecken, D. H. W., Marques, I. J., Kubutat, D., Will, J., Sheldrick, W. S., Jesse, P., Prokop, A., Bagowski, C. P. A Gold(I) Phosphine Complex Containing a Naphthalimide Ligand Functions as a TrxR Inhibiting Antiproliferative Agent and Angiogenesis Inhibitor. *J. Med. Chem.* 52, 763-770 (2009). (b) Pavic, A., Glisic, B. D., Vojnovic, S., Warzajtis, B., Savic, N. D., Antic, M., Radenkovic, S., Janjic, G. V., Nikodinovic-Runic, J., Rychlewska, U., Djuran, M. I.: Mononuclear gold(III) complexes with phenanthroline ligands as efficient inhibitors of angiogenesis: A comparative study with auranofin and sunitinib. *J. Inorg. Biochem.* 174, 156-168 (2017).

[17] Wilbuer, A., Vlecken, D. H., Schmitz, D. J., Kraling, K., Harms, K., Bagowski, C. P., Meggers, E. Iridium complex with antiangiogenic properties. *Angew. Chem. Int. Ed.* 49, 3839-3842 (2010).

[18] Zamora, A., Perez, S. A., Rodriguez, V., Janiak, C., Yellol, G. S., Ruiz, J.: Dual Antitumor and Antiangiogenic Activity of Organoplatinum(II) Complexes. *J. Med. Chem.* 58, 1320-1336 (2015).

[19] Zamora, A., Perez, S. A., Rothemund, M., Rodriguez, V., Schobert, R., Janiak, C., Ruiz, J. Exploring the Influence of the Aromaticity on the Anticancer and Antivascular Activities of Organoplatinum(II) Complexes. *Chem.-Eur. J.* 23, 5614-5624 (2017).

[20] Shojaei, F., Ferrara, N. Role of the microenvironment in tumor growth and in refractoriness/resistance to antiangiogenic therapies. *Drug Resis Update.* 11, 219-230 (2008).

[21] Gasparini, G., Longo, R., Fanelli, M., Teicher, B. A. Combination of Antiangiogenic Therapy With Other Anticancer Therapies: Results, Challenges, and Open Questions. *J. Clin. Oncol.* 23, 1295-1311 (2005).

[22] Zhang, J.-J., Sun, R. W.-Y., Che, C.-M. A dual cytotoxic and antiangiogenic water-soluble gold(III) complex induces endoplasmic reticulum damage in HeLa cells. *Chem. Commun.* 48, 3388-3390 (2012).

[23] Sun, R. W.-Y., Chow, A. L.-F., Li, X.-H., Yan, J. J., Chui, S. S.-Y., Che, C.-M. Luminescent cyclometalated platinum(II) complexes containing N-heterocyclic carbene ligands with potent in vitro and in vivo anti-cancer properties accumulate in cytoplasmic structures of cancer cells. *Chem. Sci.* 2, 728-736 (2011).

[24] Visbal, R., Gimeno, M. C. N-heterocyclic carbene metal complexes: photoluminescence and applications. *Chem. Soc. Rev.* 43, 3551-3574 (2014).

[25] Wen, H.-M., Wu, Y.-H., Fan, Y., Zhang, L.-Y., Chen, C.-N., Chen. Z.-N. Spectroscopic and Luminescence Studies on Square-Planar Platinum(II) Complexes with Anionic Tridentate 3-Bis(2-pyridylimino)isoindoline Derivatives. *Inorg. Chem.* 49, 2210-2221 (2010).

[26] Wen, H.-M., Wu, Y.-H., Xu, L.-J., Zhang, L.-Y., Chen, C.-N., Chen. Z.-N. Luminescent square-planar platinum (II) complexes with tridentate 3-bis(2-pyridylimino)isoindoline and monodentate N-heterocyclic ligands. *Dalton Trans.* 40, 6929-6938 (2011).

[27] Hanson, K., Roskop, L., Djurovich, P. I., Zahariev, F., Gordon, M. S., Thompson, M. E. A Paradigm for Blue- or Red-Shifted Absorption of Small Molecules Depending on the Site of π-Extension. *J. Am. Chem. Soc.* 132, 16247-16255 (2010).

[28] (a) C.-M. Che and F.-M. Siu, Curr. Opin. Chem. Biol., 2010, 14, 255; (b) P. C. A. Bruijnincx and P. J. Sadler, Curr. Opin. Chem. Biol., 2008, 12, 197; (c) R. W.-Y. Sun, D.-L. Ma, E. L.-M. Wong and C.-M. Che, Dalton Trans., 2007, 4884; (d) D. Wang and S. J. Lippard, Nat. Rev. Drug Discovery, 2005, 4, 307.

[29] Healy, S. J., Gorman, A. M., Mousavi-Shafaei, P., Gupta, S., Samali, A. Targeting the endoplasmic reticulum-stress response as an anticancer strategy. *Eur. J. Pharmacol.* 625, 234-246 (2009).

[30] Lai, E., Teodoro, T., Volchuk, A. Endoplasmic reticulum stress: signaling the unfolded protein response. *Physiology.* 22, 193-201 (2007).

[31] Smiley, S. T., Reers, M., Mottola-Hartshorn, C.; Lin, M., Chen, A., Smith, T. W.; Steele, G. D.; Chen, L. B. Intracellular Heterogeneity in Mitochondrial Membrane Potentials Revealed by a J-Aggregate-Forming Lipophilic Cation JC-1. *Proc. Natl. Acad. Sci. U.S.A* 88, 3671-3675 (1991).

[32] Sun, C., Li, H. L., Chen, H. R., Shi, M. L., Liu, Q. H., Pan, Z. Q., Bai, J., Zheng. J. N. Decreased expression of CHIP leads to increased angiogenesis via VEGF-VEGFR2 pathway and poor prognosis in human renal cell carcinoma. *Sci. Reports.* 5, 9774 (2015)

[33] Shiao, Y. H. The von Hippel-Lindau gene and protein in tumorigenesis and angiogenesis: a potential target for therapeutic designs. *Curr Med. Chem.* 10, 2461-2470 (2003).

[34] Liang, J., Wu, Y. L., Chen, B. J., Zhang, W., Tanaka, Y., Sugiyama, H. The C-Kit Receptor-Mediated Signal Transduction and Tumor-Related Diseases. *Int. J. Bio. Sci.* 9, 435-443 (2013).
[35] Kessenbrock, K., Plaks, V., Werb, Z. Matrix Metalloproteinases: Regulators of the Tumor Microenvironment. *Cell.* 141, 52-67 (2010).
[36] Hwang, K. E., Shon, Y. J., Cha, B. K., Park, M. J., Chu, M. S., Kim, Y. J., Jeong, E. T., Kim, H. R. Tissue inhibitor of metalloproteinase-1 is responsible for residual pleural thickening in pleural tuberculosis. Tohoku. *J. Exp. Med.* 235, 327-333 (2015).
[37] Gondi, C. S., Kandhukuri, N., Dinh, D. H., Gujrati, M., Rao, J. S. Down-regulation of uPAR and uPA activates caspase-mediated apoptosis and inhibits the PI3K/AKT pathway. *Int. J. Oncol.* 31, 19-27 (2007).
[38] Vial, E., Sahai, E., Marshall, C. J. ERK-MAPK signaling coordinately regulates activity of Rac1 and RhoA for tumor cell motility. *Cancer Cell.* 4, 67-79 (2003).
[39] Walker, E. H., Pacold, M. E., Perisic, O., Stephens, L., Hawkins, P. T., Wymann, M. P., Williams, R. L. Structural Determinants of Phosphoinositide 3-Kinase Inhibition by Wortmannin, LY294002, Quercetin, Myricetin, and Staurosporine. *Mol. Cell.* 6, 909-919 (2000).
[40] Marampon, F., Bossi, G., Ciccarelli, C., Di Rocco, A., Sacchi, A., Pestell, R. G., Zani, B. M. MEK/ERK inhibitor U0126 affects in vitro and in vivo growth of embryonal rhabdomyosarcoma. *Mol. Cancer. Ther.* 8, 543-551 (2009).
[41] Hicklin, D. J., Ellis, L. M. Role of the vascular endothelial growth factor pathway in tumor growth and angiogenesis. *J. Clin. Oncol.* 23, 1011-1027 (2005).
[42] Ferrara, N., Gerber, H. P., LeCouter, J. The biology of VEGF and its receptors. *Nat. Med.* 9, 669-676 (2003).
[43] Plouet. J., Moro. F., Bertagnolli. S., et al. Extracellular cleavage of the vascular endothelial growth factor 189-amino acid form by urokinase is required for its mitogenic effect. *J. Biol. Chem.* 272, 13390-13396 (1997).
[44] Rodriguez-Manzaneque, J. C., Lane, T. F., Ortega, M. A., Hynes, R. O., Lawler, J., Iruela-Arispe, M. L. Thrombospondin-1 suppresses spontaneous tumor growth and inhibits activation of matrix metalloproteinase-9 and mobilization of vascular endothelial growth factor. *Proc. Natl. Acad. Sci.* 98, 12485-12490 (2001).
[45] Mira, E., Lacalle, R. A., Buesa, J. M., et al. Secreted MMP9 promotes angiogenesis more efficiently than constitutive active MMP9 bound to the tumor cell surface. *J. Cell. Sci.* 117, 1847-1857 (2004).
[46] Irina A., Hynda K. K. In vitro angiogenesis: endothelial cell tube formation on gelled basement membrane extract. *Nat. Protocols* 5, 628-635 (2010).
[47] H.-M. Wen, Y.-H. Wu, Y. Fan, L.-Y. Zhang, C.-N. Chen, Z.-N. Chen, *Inorg. Chem.* 2010, 49, 2210-2221.
[48] R. A. Zubarev, M. L. Nielsen, E. M. Fung, M. M. Savitski, O. Kel-Margoulis, E. Wingender, A. Kel, *J. Proteomics* 2008, 71, 89.
[49] S.-T. Lau, T. Zhou, J. A.-J. Liu, E. Y.-M. Fung, C.-M. Che, B. H.-H. Lang, E. S.-W. Ngan, *Biochim. Biophys. Acta, Mol. Basis Dis.* 2015, 1852, 1676.

What is claimed is:

1. A Pt(II) complex of formula I:

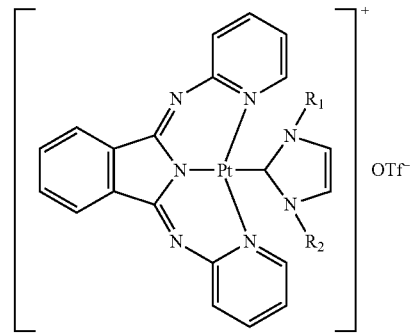

wherein $R^1$ is —$CH_3$, —$C_4H_9$, -$nC_6H_{13}$, —$CH_3$, or —$CH_2Ph$, and wherein $R^2$ is —$CH_3$, —$C_4H_9$, -$nC_6H_{13}$, —$C_8H_{17}$, —$C_{16}H_{33}$, or —$CH_2Ph$.

2. The Pt(II) complex of claim 1 wherein the Pt(II) complex has anti-tumor or anti-angiogenic properties.

3. A composition comprising the Pt(II) complex of claim 1.

4. The composition of claim 3 wherein the Pt(II) complex comprises anti-tumor and/or anti-angiogenic properties.

* * * * *